US008823934B2

(12) United States Patent  
Chhibber et al.

(10) Patent No.: US 8,823,934 B2  
(45) Date of Patent: *Sep. 2, 2014

(54) METHODS AND SYSTEMS FOR IMAGING AND MODELING SKIN USING POLARIZED LIGHTING

(75) Inventors: Rajeshwar Chhibber, San Jose, CA (US); Ashutosh Chhibbar, San Jose, CA (US); Shefali Sharma, Petaluma, CA (US)

(73) Assignee: Brightex Bio-Photonics LLC, San Jose, CA (US)

( * ) Notice: Subject to any disclaimer, the term of this patent is extended or adjusted under 35 U.S.C. 154(b) by 506 days.

This patent is subject to a terminal disclaimer.

(21) Appl. No.: 13/078,834

(22) Filed: Apr. 1, 2011

(65) Prior Publication Data

US 2011/0211047 A1 Sep. 1, 2011

Related U.S. Application Data

(63) Continuation-in-part of application No. 12/731,072, filed on Mar. 24, 2010, now Pat. No. 8,373,859.

(60) Provisional application No. 61/320,627, filed on Apr. 2, 2010, provisional application No. 61/164,356, filed on Mar. 27, 2009.

(51) Int. Cl.  
*G01J 4/00* (2006.01)  
*G06K 9/62* (2006.01)

(52) U.S. Cl.  
USPC ........... 356/366; 356/364; 356/367; 356/368; 382/165

(58) Field of Classification Search  
USPC ................. 356/364–369; 348/77, 187, 211.3, 348/222.1, 370; 434/377, 99, 100, 371; 382/128, 165, 154, 124, 125; 600/476, 600/410, 425

See application file for complete search history.

(56) References Cited

U.S. PATENT DOCUMENTS

| 4,151,512 A | 4/1979 | Riganati et al. ........ 340/146.3 E |
| 4,186,378 A | 1/1980 | Moulton ................ 340/146.3 E |
| 4,236,082 A | 11/1980 | Butler ........................ 250/461 R |
| 4,871,262 A | 10/1989 | Krauss et al. ................. 366/160 |

(Continued)

FOREIGN PATENT DOCUMENTS

WO    WO 90/13091 A1    11/1990

OTHER PUBLICATIONS

Brightex Bio-Photonics, IPRP, PCT/US2011/031065, Oct. 11, 2012, 11 pgs.

(Continued)

*Primary Examiner* — Sang Nguyen  
(74) *Attorney, Agent, or Firm* — Ward & Zinna, LLC

(57) ABSTRACT

A method for imaging skin includes illuminating a subject with at least one light source of one or more light sources. The method includes acquiring a first image of the subject in a first polarization with a respective photodetector of one or more photodetectors configured to acquire images of the subject as illuminated by the at least one light source, and acquiring a second image of the subject in a second polarization with the respective photodetector. The method also includes generating a subtraction image by subtracting at least a portion of the first image from a corresponding portion of the second image, and providing at least a portion of the subtraction image for display.

20 Claims, 21 Drawing Sheets

(56) References Cited

U.S. PATENT DOCUMENTS

| | | | | |
|---|---|---|---|---|
| 4,894,547 A | 1/1990 | Leffell et al. | | 250/461.2 |
| 5,074,306 A | 12/1991 | Green et al. | | 128/664 |
| 5,343,536 A | 8/1994 | Groh | | 382/6 |
| 5,363,854 A | 11/1994 | Martens et al. | | 128/665 |
| 5,818,954 A | 10/1998 | Tomono et al. | | 382/115 |
| 5,836,872 A | 11/1998 | Kenet et al. | | 600/306 |
| 5,862,247 A | 1/1999 | Fisun et al. | | 382/116 |
| 6,021,344 A | 2/2000 | Lui et al. | | 600/476 |
| 6,032,071 A | 2/2000 | Binder | | |
| 6,061,463 A | 5/2000 | Metz et al. | | 382/124 |
| 6,069,689 A | 5/2000 | Zeng et al. | | 356/73 |
| 6,081,612 A | 6/2000 | Gutkowicz-Krusin et al. | | |
| 6,141,434 A | 10/2000 | Christian et al. | | 382/103 |
| 6,317,624 B1 | 11/2001 | Kollias et al. | | 600/476 |
| 6,475,153 B1 | 11/2002 | Khair et al. | | 600/485 |
| 6,533,729 B1 | 3/2003 | Khair et al. | | 600/503 |
| 6,556,708 B1 | 4/2003 | Christian et al. | | 382/165 |
| 6,571,003 B1 | 5/2003 | Hillebrand et al. | | 382/118 |
| 6,587,711 B1 | 7/2003 | Alfano et al. | | 600/476 |
| 6,611,622 B1 | 8/2003 | Krumm | | 382/170 |
| 6,763,262 B2 | 7/2004 | Hohla et al. | | 600/476 |
| 6,782,307 B2 | 8/2004 | Wilmott et al. | | 700/233 |
| 6,907,138 B1 * | 6/2005 | Hoffman et al. | | 382/154 |
| 7,217,266 B2 | 5/2007 | Anderson et al. | | |
| 7,233,693 B2 | 6/2007 | Momma | | 382/162 |
| 7,289,211 B1 | 10/2007 | Walsh, Jr. et al. | | |
| 7,349,857 B2 | 3/2008 | Manzo | | 705/2 |
| 7,369,692 B2 | 5/2008 | Shirai et al. | | 382/128 |
| 7,454,046 B2 | 11/2008 | Chhibber et al. | | 382/128 |
| 7,460,248 B2 | 12/2008 | Kurtz et al. | | 356/521 |
| 7,477,767 B2 | 1/2009 | Chhibber et al. | | 382/128 |
| 7,627,151 B2 * | 12/2009 | Rowe | | 382/124 |
| 7,840,064 B2 | 11/2010 | Chhibber et al. | | 382/165 |
| 8,131,029 B2 | 3/2012 | Chhibber et al. | | |
| 2003/0223083 A1 | 12/2003 | Geng | | 356/603 |
| 2004/0111031 A1 | 6/2004 | Alfano et al. | | |
| 2004/0125996 A1 | 7/2004 | Eddowes et al. | | 382/128 |
| 2004/0179719 A1 | 9/2004 | Chen et al. | | 382/118 |
| 2004/0249274 A1 | 12/2004 | Yaroslavsky et al. | | 600/431 |
| 2005/0008199 A1 | 1/2005 | Dong et al. | | 382/115 |
| 2005/0046830 A1 | 3/2005 | Karp et al. | | 356/237.1 |
| 2005/0195316 A1 | 9/2005 | Kollias et al. | | 348/370 |
| 2006/0092315 A1 | 5/2006 | Payonk et al. | | 348/370 |
| 2006/0182323 A1 | 8/2006 | Kollias et al. | | 382/128 |
| 2007/0002479 A1 | 1/2007 | Menke et al. | | 359/892 |
| 2007/0004972 A1 | 1/2007 | Cole et al. | | 600/306 |
| 2007/0064978 A1 | 3/2007 | Chhibber et al. | | 382/118 |
| 2007/0064979 A1 | 3/2007 | Chhibber et al. | | 382/118 |
| 2008/0051773 A1 | 2/2008 | Ivanov et al. | | |
| 2008/0212894 A1 | 9/2008 | Demirli et al. | | |
| 2009/0136101 A1 | 5/2009 | Chhibber et al. | | 382/128 |
| 2009/0141956 A1 | 6/2009 | Chhibber et al. | | 382/128 |
| 2009/0196475 A1 | 8/2009 | Demirli et al. | | 382/128 |
| 2010/0309300 A1 | 12/2010 | Chhibber et al. | | 348/77 |
| 2010/0316296 A1 | 12/2010 | Chhibber et al. | | 382/190 |

OTHER PUBLICATIONS

Anonymous, *Build Your Own 3D Scanner w/Structured Light*, Nov. 23, 2009, 7 pgs.

Anonymous, *Stereo Accuracy and Error Modeling*, Point Grey Research Inc., Apr. 19, 2004, 3 pgs.

Basset, *Application of texture analysis for the classification of bovine meat*, Food Chemistry 69, 2000, pp. 437-445.

Blanz, *A Morphable Model for the Synthesis of 3D Faces*, SIGGRAPH '99, Losa Angeles CA, 1999, pp. 187-194.

Fulton, *Utilizing the Ultraviolet (UV Detect) Camera to Enhance the Appearance of Photodamage and Other Skin Conditions*, American Society for Dermatologic Surgery, 1997, pp. 163-169.

Hsu, *Face Detection in Color Images*, IEEE Transactions on Pattern Analysis and Machine Intelligence, vol. 24, No. 5, May 2002, pp. 696-706.

International Search Report and Written Opinion, PCT/2006/036696, Nov. 6, 2007, 5 pgs.

International Search Report and Written Opinion, PCT/2010/028617, May 20, 2010, 7 pgs.

Kollias, *Optical Non-Invasive Approaches to Diagnosis of Skin Diseases*, JID Symposium Proceedings, 2002, pp. 64-75.

Liangen, *Human Skin Surface Evaluation by Image Processing*, SPIE vol. 5254, 3rd Int'l Conference on Photonics and Imaging in Biology and Medicine, Bellingham WA, 2003, pp. 362-367.

Rosco color filter technical data sheet, 2001, 2 pgs.

Sandby-Moller, *Influence of epidermal thickness, pigmentation and redness on skin autofluorescence*, American Society of Photobiology, Jun. 2003, pp. 1-9.

Sboner, *Clinical validation of an automated system for supporting the early diagnosis of melanoma*, Skin Research and Technology, vol. 10, 2004, pp. 184-192.

Zeng, *Autofluorescence properties of skin and application in dermatology*, Proceedings of SPIE, Bol. 4224, 2000, pp. 366-373.

Zhang, *3-D Face Structure Extraction and Recognition From Images Using 3-D Morphing and Distance Mapping*, IEEE Transactions on Image Processing, vol. 11, No. 11, Nov. 2002, 1249-1259.

International Search Report and Written Opinion for PCT/US2011/031065 dated Jun. 20, 2011, 11 pgs.

\* cited by examiner

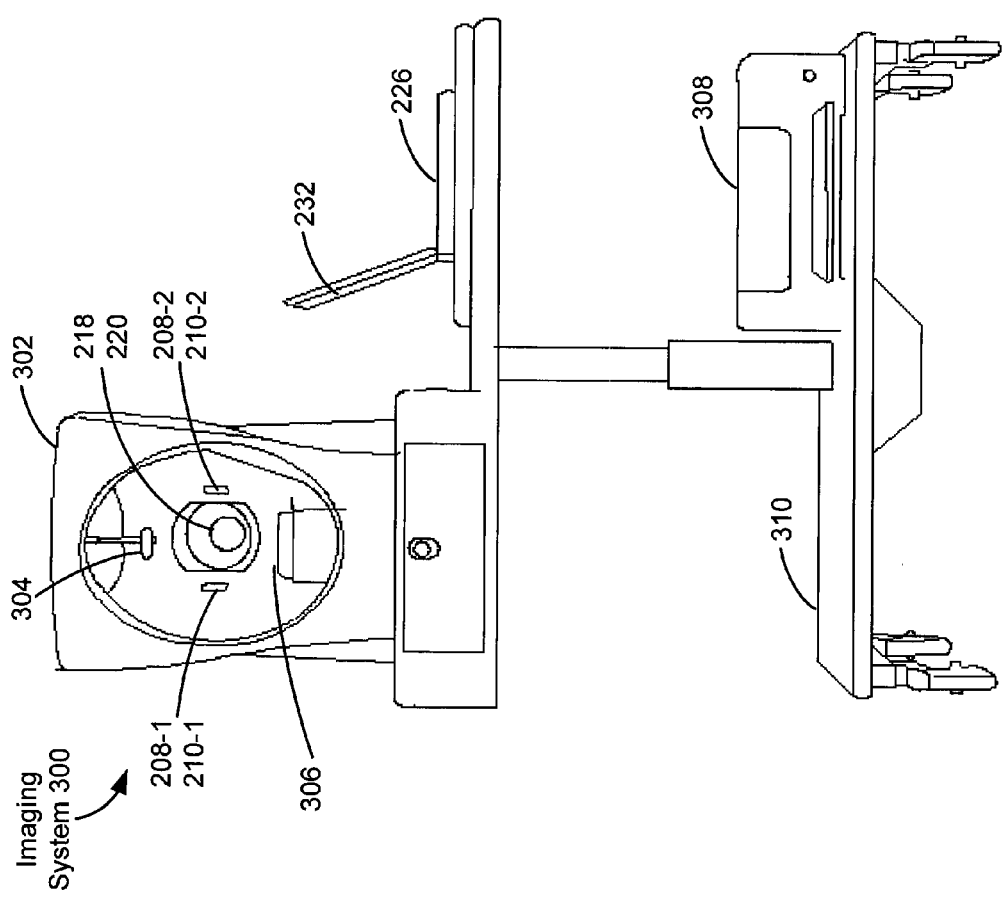

Skin Condition Table
600

| | Name | Min. Color Value | Max. Color Value | Min. Intensity Value | Max. Intensity Value |
|---|---|---|---|---|---|
| Condition 1 | Name | Min. Color Value | Max. Color Value | Min. Intensity Value | Max. Intensity Value |
| Condition 2 | Name | Min. Color Value | Max. Color Value | Min. Intensity Value | Max. Intensity Value |

Figure 6A

Cosmetic Product Recommendation Table
630

| | Product | Min. Color Value | Max. Color Value | Min. Intensity Value | Max. Intensity Value |
|---|---|---|---|---|---|
| | Product | Min. Color Value | Max. Color Value | Min. Intensity Value | Max. Intensity Value |
| | Product | Min. Color Value | Max. Color Value | Min. Intensity Value | Max. Intensity Value |

Receive a first image of a subject. The first image was acquired at an imaging apparatus with the subject illuminated with light having a first polarization and the imaging apparatus configured to receive light having the first polarization and to otherwise reject light.

744

Receive a second image of the subject. The second image was acquired at the imaging apparatus with the subject illuminated with light having the first polarization and the imaging apparatus configured to at least partially reject light having the first polarization and to at least partially receive light having polarization distinct from the first polarization.

746

Subtract the first image from the second image to generate a third image of the subject.

748

Displaying the third image.

Figure 7D

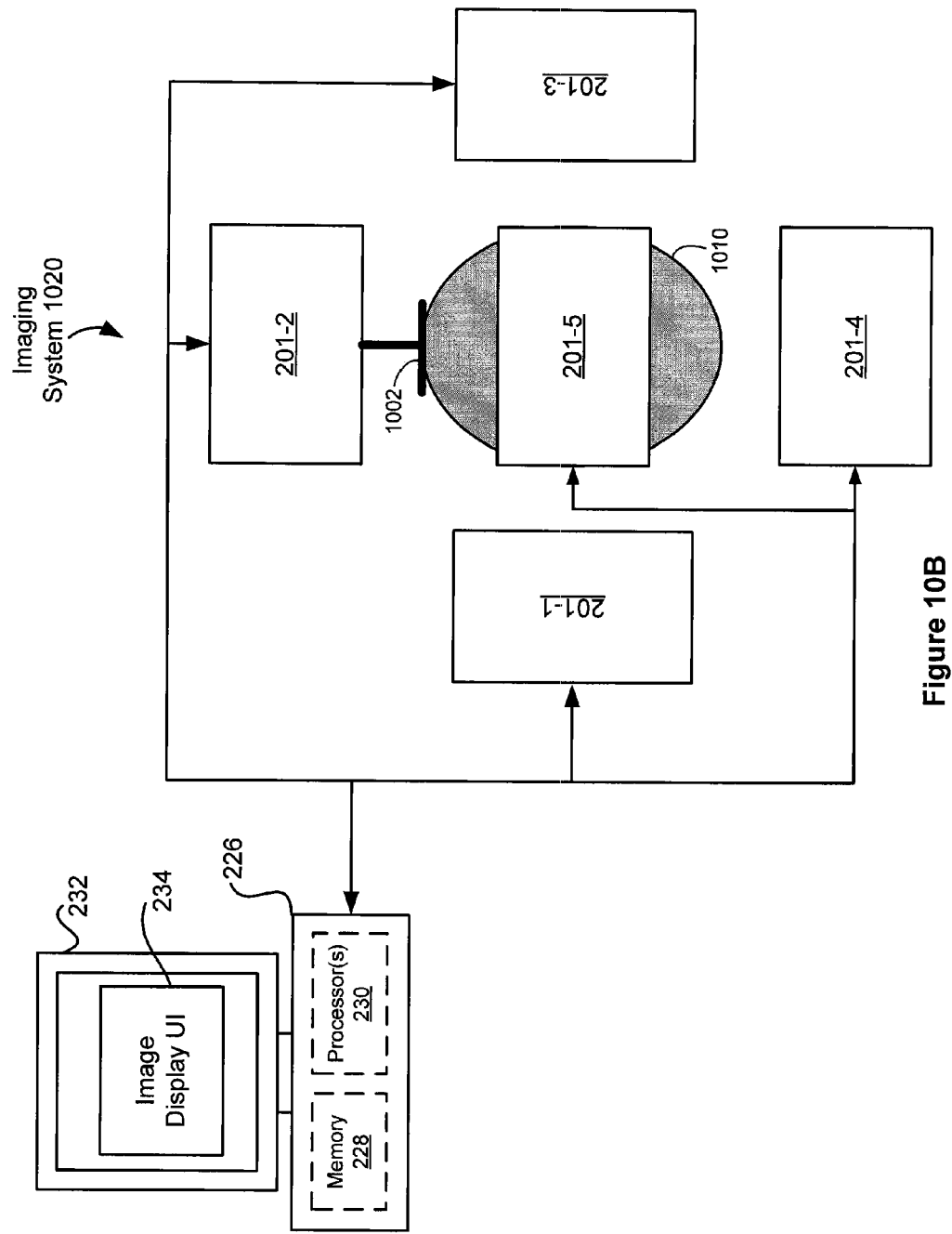

1100

1102 Illuminate the subject with at least one light source of one or more light sources

1104 The one or more light sources include at least one polarizer to polarize light provided by at least one of the one or more light sources to illuminate the subject

1106 Acquire a first image of the subject in a first polarization with a respective photodetector of one or more photodetectors configured to acquire images of the subject as illuminated by the at least one light source

1108 Acquire a second image of the subject in a second polarization with the respective photodetector

1110 The subject is illuminated with light polarized in the first polarization. The first image of the subject in the first polarization is acquired with the respective photodetector while a respective adjustable polarizer coupled with the respective photodetector is configured to provide a first axis of polarization such that the respective adjustable polarizer transmits the light polarized in the first polarization; and the second image of the subject in the second polarization is acquired with the respective photodetector while the respective adjustable polarizer coupled with the respective photodetector is configured to provide a second axis of polarization distinct from the first axis of polarization such that the respective adjustable polarizer rejects the light polarized in the first polarization.

1112 The subject is illuminated with light polarized in the first polarization; the first image of the subject in the first polarization is acquired with the respective photodetector while a respective adjustable polarizer coupled with the respective photodetector is configured to provide a first axis of polarization such that the respective adjustable polarizer rejects the light polarized in the first polarization; and the second image of the subject in the second polarization is acquired with the respective photodetector while the respective adjustable polarizer coupled with the respective photodetector is configured to provide a second axis of polarization distinct from the first axis of polarization such that the respective adjustable polarizer transmits the light polarized in the first polarization.

1126 Acquire with a first photodetector a third image of the subject illuminated with a first image pattern of one or more image patterns from a first light source; acquire with a second photodetector a fourth image of the subject illuminated with the first image pattern of the one or more image patterns from the first light source; acquire with the second photodetector a fifth image of the subject illuminated with a second image pattern of the one or more image patterns from the second light source; acquire with a third photodetector a sixth image of the subject illuminated with the second image pattern of the one or more image patterns from the second light source; generate a three-dimensional model corresponding to at least a portion of the subject by comparing at least a portion of the third image and at least a portion of the fourth image, and comparing at least a portion of the fifth image and at least a portion of the sixth image; and
map at least a portion of the subtraction image onto the three-dimensional model.

1128 The first image pattern and the second image pattern are identical.

Figure 11C

METHODS AND SYSTEMS FOR IMAGING AND MODELING SKIN USING POLARIZED LIGHTING

RELATED APPLICATIONS

This application claims priority to U.S. Provisional Application Ser. No. 61/320,627, filed Apr. 2, 2010, entitled "Methods and Systems for Imaging and Modeling Skin Using Polarized Lighting," which is incorporated by reference herein in its entirety. This application is a continuation-in-part of U.S. patent application Ser. No. 12/731,072, filed Mar. 24, 2010 now U.S. Pat. No. 8,373,859, entitled "Methods and Systems for Imaging Skin Using Polarized Lighting," which claims priority to U.S. Provisional Application Ser. No. 61/164,356, filed Mar. 27, 2009, entitled "Methods and Systems for Imaging Skin Using Polarized Lighting." All of these applications are incorporated by reference herein in their entireties.

TECHNICAL FIELD

The disclosed embodiments relate generally to imaging skin, and more particularly, to imaging skin using polarized lighting and generating models of the imaged skin.

BACKGROUND

High-quality images of a subject's skin have potential applications in dermatology and cosmetics, among other fields. Obtaining high-quality skin images, however, presents significant engineering challenges. For example, skin conditions on the surface of the skin, such as wrinkles, can interfere with imaging sub-surface features. In another example, skin care products can interfere with images taken using fluorescence techniques.

SUMMARY

In some embodiments, an imaging system for imaging skin includes a light source to illuminate a subject, a first polarizer to polarize light provided by the light source to illuminate the subject, and a filter to filter out red light. The imaging system also includes a photodetector to acquire an image of the subject as illuminated by the light source and an adjustable second polarizer, coupled to the photodetector, to provide an adjustable axis of polarization of light received by the photodetector.

In some embodiments, an imaging system includes a plurality of imaging apparatuses to acquire images of a subject. Respective apparatuses of the plurality are positioned to record respective images of the subject from respective angles. Each imaging apparatus of the plurality includes a light source to illuminate the subject, a first polarizer to polarize light provided by the light source to illuminate the subject, and a photodetector to acquire an image of the subject as illuminated by the light source. Each imaging apparatus of the plurality also includes an adjustable second polarizer, coupled to the photodetector, to provide an adjustable axis of polarization of light received by the photodetector.

In some embodiments, a method of imaging skin includes illuminating a subject with polarized light having a first polarization. A polarizer is adjusted to reject light having the first polarization and to admit light having polarization distinct from the first polarization onto a photodetector. An image of the illuminated subject is acquired using the photodetector.

In some embodiments, a method of generating a sub-surface skin image includes illuminating a subject with polarized light having a first polarization. An adjustable polarizer is set to a first setting to admit light having the first polarization onto a photodetector and otherwise reject light. With the adjustable polarizer in the first setting, the photodetector is used to acquire a first image of the illuminated subject. The adjustable polarizer is set to a second setting to at least partially reject light having the first polarization and to at least partially admit light having polarization distinct from the first polarization onto the photodetector. With the adjustable polarizer in the second setting, the photodetector is used to acquire a second image of the illuminated subject. The first image is subtracted from the second image to generate a third image of the subject.

In some embodiments, a method for imaging skin, performed by a system including one or more processors and memory storing one or more programs for execution by the one or more processors, includes illuminating a subject with at least one light source of one or more light sources; acquiring a first image of the subject in a first polarization with a respective photodetector of one or more photodetectors configured to acquire images of the subject as illuminated by the at least one light source; and acquiring a second image of the subject in a second polarization with the respective photodetector. The method includes generating a subtraction image by subtracting at least a portion of the first image from a corresponding portion of the second image; and providing at least a portion of the subtraction image for display.

In some embodiments, an imaging system for imaging skin includes: one or more light sources configured to illuminate a subject; one or more photodetectors configured to acquire images of the subject as illuminated by at least one of the one or more light sources; and one or more adjustable polarizers. Each adjustable polarizer is coupled with a respective photodetector of the one or more photodetectors and configured to provide an adjustable axis of polarization of light received by the respective photodetector. The imaging system includes one or more processors; and memory storing one or more programs for execution by the one or more processors. The one or more programs include instructions for: acquiring a first image of the subject in a first polarization with the respective photodetector; acquiring a second image of the subject in a second polarization with the respective photodetector; generating a subtraction image by subtracting at least a portion of the first image from a corresponding portion of the second image; and providing at least a portion of the subtraction image for display.

BRIEF DESCRIPTION OF THE. DRAWINGS

FIG. 3 is a diagram illustrating an imaging system including a light box in accordance with some embodiments.

FIGS. 6A and 6B are diagrams illustrating data structures for analyzing images of skin in accordance with some embodiments.

FIG. 7D is a flow diagram illustrating a computer-implemented method of processing and displaying images of skin in accordance with some embodiments.

FIGS. 10A-10C are block diagrams illustrating imaging systems in accordance with some embodiments.

FIGS. 11A-11C are flow diagrams illustrating a method of imaging skin in accordance with some embodiments.

Like reference numerals refer to corresponding parts throughout the drawings.

DESCRIPTION OF EMBODIMENTS

Reference will now be made in detail to embodiments, examples of which are illustrated in the accompanying drawings. In the following detailed description, numerous specific details are set forth in order to provide a thorough understanding of the present inventions. However, it will be apparent to one of ordinary skill in the art that the present inventions may be practiced without these specific details. In other instances, well-known methods, procedures, components, and circuits have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first image could be termed a second image, and, similarly, a second image could be termed a first image, without departing from the scope of the present invention. The first image and the second image are both images, but they are not the same image.

Figure 1A:
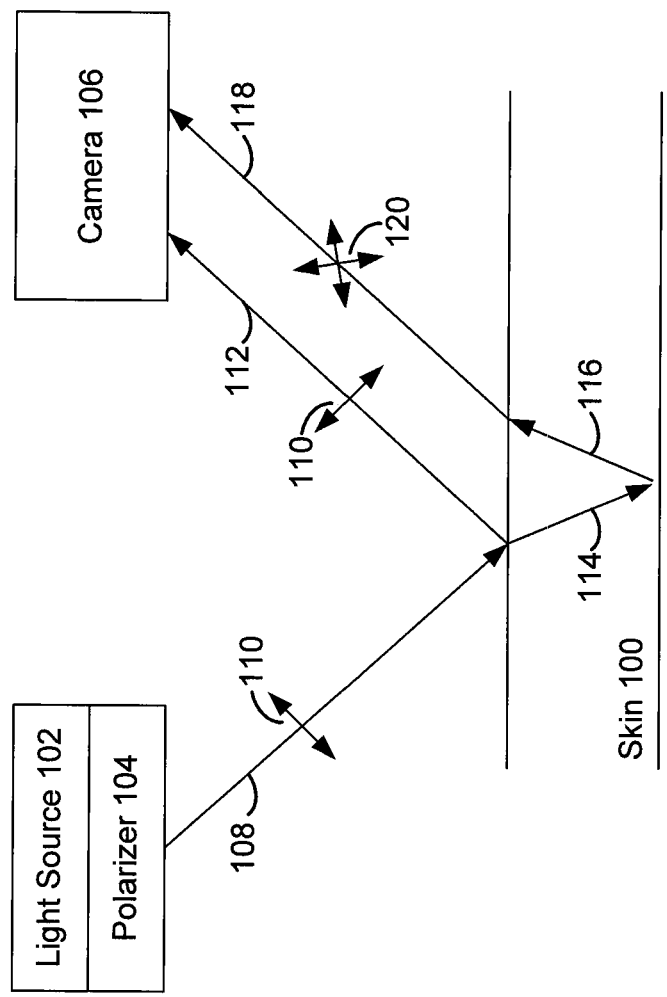
FIGS. 1A-1B are schematic cross-sectional views of polarized light incident on and reflected from skin in accordance with some embodiments.

FIG. 1A is a schematic cross-sectional view of polarized light incident on and reflected from skin in accordance with some embodiments. A light source 102 is covered by a polarizer 104, such that light 108 illuminating skin 100 has a particular polarization 110. In the example of FIG. 1A, the polarizer 104 is a linear polarizer and the light 108 is linearly polarized (i.e., polarization 110 is linear polarization). Light 112 is reflected from the surface of the skin 100 and detected by a camera (e.g., a digital camera) 106. The light 112 reflected from the surface of the skin 100 has the same polarization 110 as the incident light 108 and thus is also linearly polarized. Not all of the incident light 108 is reflected from the surface of the skin 100, however. A portion 114 of the incident light 108 penetrates to a particular depth within the skin 100 before being reflected. (For simplicity, FIG. 1A shows incident light 108 penetrating to a single depth within the skin 100 before being reflected as light 116 and 118. In reality, incident light 108 penetrates to a range of depths before being reflected.) The light 118 reflected from beneath the surface of the skin 100 has a polarization (e.g., an elliptical polarization) 120 distinct from the polarization 110 of the light 112 reflected from the surface of the skin 100. In general, the polarization 120 of the light 118 is random.

The camera 106 thus receives partially polarized light: a portion of the received light has the polarization 110, and thus corresponds to light 112 reflected from the surface of the skin 100, while another portion has essentially random polarization 120, and thus corresponds to light 118 reflected from beneath the surface of the skin 100.

The camera 106 may be equipped with a polarizer which may be configured (e.g., by rotating the polarizer) to (1) admit only light having the polarization 110, such that all other polarizations are rejected, (2) reject all light having the polarization 110, such that admitted light is polarized perpendicular to the polarization 110, or (3) admit partially polarized light that includes components having the polarization 110 and components having a polarization perpendicular to the polarization 110. In the first case, an image taken by the camera 106 corresponds to light reflected from the surface of the skin 100 and is thus an image of the surface of the skin 100. In the second case, an image taken by the camera 106 corresponds to light reflected from a depth beneath the surface of the skin 100 that varies from approximately 350 microns for very dark skin (e.g., Type 6 skin on the Fitzpatrick scale) to approximately 3 mm for very fair skin (e.g., Type 1 skin on the Fitzpatrick scale). The image in the second case is thus a sub-surface image of the skin 100. In the third case, an image taken by the camera 106 corresponds to light reflected from both the surface and from varying depths beneath the surface of the skin 100 and thus can be considered a combination of surface and sub-surface skin images.

Figure 1B:
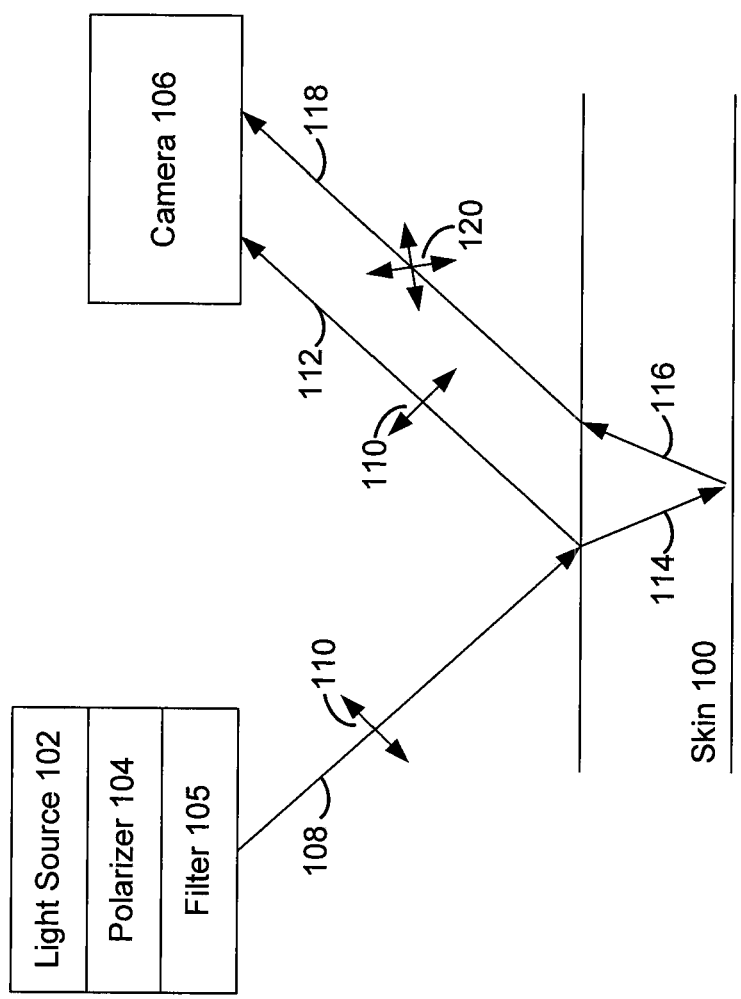

In FIG. 1B, the light source 102 is covered by a filter 105 as well as the polarizer 104. The filter 105 filters out red light (i.e., blocks light with wavelengths in the red portion of the visual spectrum, for example, light with wavelengths between approximately 550 nm and 700 nm) while transmitting light at other wavelengths (e.g., blue light). Because red light does not penetrate as deep into skin as other wavelengths of light, filtering out red light enhances the ability of the camera 106 to take images that correspond at least partially to light reflected from beneath the surface of the skin 100. For example, when the filter 105 is used to filter red light from the light source 102 and the polarizer of the camera 106 is configured to reject all light having the polarization 110, such that admitted light is polarized perpendicular to the polarization 110, an image taken by the camera 106 corresponds to light reflected from a depth of 2 mm or more even for very dark skin (e.g., Type 5 or Type 6 skin). However, the filter 105 is omitted when using the camera 106 to image blood vessels.

Referring to the component of received light with the polarization 110 as PAR (i.e., polarized parallel to a plane of polarization of the incident light 108) and to the component of received light polarized perpendicular to the plane of polarization of the incident light 108 as PER, the degree of partial polarization of light admitted by the polarizer and thus imaged by the camera 106 can be quantified as:

$$\text{Degree of Partial Polarization} = (PAR - PER)/(PAR + PER) \quad (1)$$

This formula thus quantifies the percentage of light admitted by the polarizer that corresponds to light reflected from the surface of the skin 100 as opposed to light reflected from beneath the surface of the skin 100.

Figure 2A:
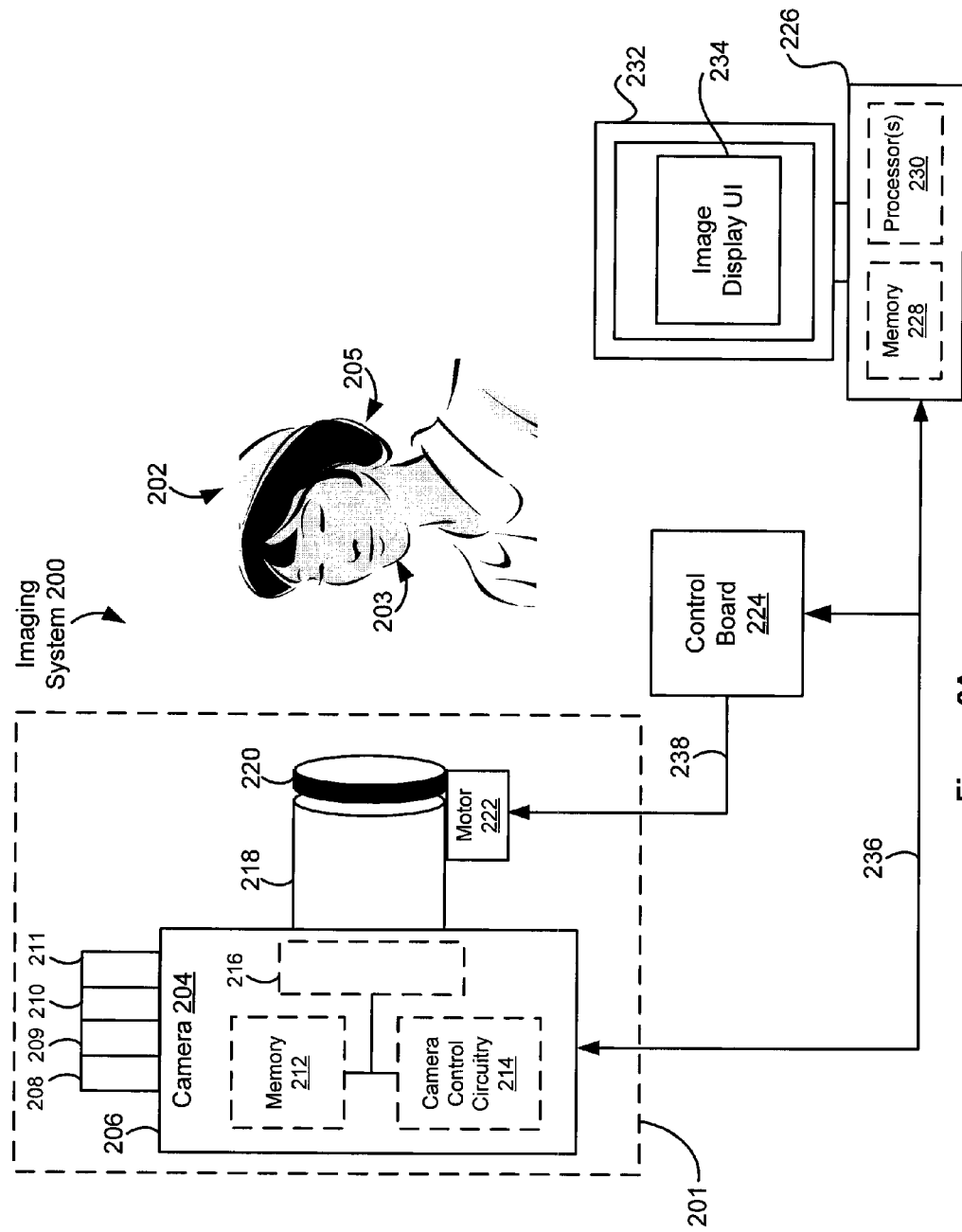
FIGS. 2A-2C are block diagrams of imaging systems for imaging skin in accordance with some embodiments.

FIG. 2A is a block diagram of an imaging system 200 for imaging skin 203 of a subject 202 in accordance with some embodiments. The imaging system 200 images the skin 203 in accordance with the physical principles illustrated in FIGS. 1A-1B. While the system 200 is illustrated as imaging human facial skin, in some embodiments the system 200 may be used to image any type of animal skin or to image hair as well as skin. In the system 200, an imaging apparatus 201 includes a camera (e.g., a digital camera) 204. The camera 204, which is an example of a camera 106 (FIG. 1), includes a photodetector 216 to acquire images of the subject 202, computer memory 212 to store acquired images, and camera control circuitry 214 (e.g., one or more processors) to control acquisition and storage of the images. The photodetector 216, memory 212, and control circuitry 214 are contained in a housing 206 of the camera. In some embodiments, the photodetector 216 comprises an array of charge-coupled devices (CCD), charge-injection devices (CID), or CMOS devices. In some embodiments, the photodetector 216 includes 5-15 or more megapixels. In some embodiments, each pixel includes three sub-pixels corresponding to three distinct color channels (e.g., red, green, and blue, or alternatively, a set of colors associated with another color space). In some embodiments, the photodetector 216 is rotatable to provide a variable aspect ratio for acquired images. Rotation of the photodetector 216 is controlled, for example, by the control circuitry 214.

The system 200 includes one or more light sources 208 (hereinafter, "light sources 208") to illuminate the subject 202 and one or more polarizers 210 (hereinafter, "polarizers 210") to polarize the light from the light sources 208 illuminating the subject 202. The light sources 208 and polarizers 210 are examples of the light source 102 and polarizer 104 (FIGS. 1A-1B). In some embodiments, the light sources 208 and polarizers 210 are coupled to the camera housing. For example, the light sources 208 and polarizers 210 are affixed to the camera housing 206, as illustrated in FIG. 2A, or integrated into the camera housing 206. Alternatively, the light sources 208 and polarizers 210 are physically separate from the camera 204. In some embodiments, the light sources 208 include one or more flash bulbs, one or more light-emitting diodes (LEDs), or one or more fluorescent high-temperature white-light sources. In some embodiments, when the light sources 208 include one or more light sources, such as an LED, that are configured to emit polarized light, the system do not include the polarizers 210. In some embodiments, the polarizers 210 include one or more linear polarizers. If multiple polarizers 210 are present, the multiple polarizers 210 are aligned to provide the same polarization. In some embodiments, the polarizers 210 are fixed, such that the polarization they provide is not adjustable. A polarizer 210 may be mounted on a respective light source 208 or otherwise arranged such that it polarizes light from the light source 208 that is incident on the subject 202.

In some embodiments, one or more filters 209 (hereinafter, "filters 209"), which are examples of filters 105 (FIG. 1B), are situated in-line with respective light sources 208 and polarizers 210, to filter out red light from the light provided by the light sources 208 to illuminate the subject. Examples of filters 209 include Rosco E-Colour filters #195 ("Zenith Blue") and #115 ("Peacock Blue") and Rosco Roscolux filters #73 ("Peacock Blue") and #370 ("Italian Blue"). The filters 209 are affixed to the camera housing 206 along with the light sources 208 and polarizers 210, as illustrated in FIG. 2A, or integrated into the camera housing 206. For example, the filters 209 are affixed to the camera housing 206 such that they can be flipped in or out of position, to either filter or not filter light from the light sources 208, respectively. The filters 209 are flipped into position when imaging deep sub-surface skin features, particularly for subjects with dark skin (e.g., Types 4, 5, or 6) and are flipped out of position to image blood vessels and associated perfusion. Alternatively, in embodiments in which the light sources 208 and polarizers 210 are physically separate from the camera 204, the filters 209 also are physically separate from the camera 204.

In some embodiments, a patterned substrate 211 is situated in-line with a light source 208, polarizer 210, and (optionally) filter 209. When the subject 202 is illuminated through the patterned substrate 209, a light pattern is produced on the subject 202 (e.g., on the face of the subject 202). For example, the substrate 209 is patterned with a grid (e.g., a checkerboard) that produces the appearance of a grid of light lines on the subject 202, or is patterned with an array of points (e.g., the substrate is opaque except for an array of transparent points) that produces the appearance of an array of points of light on the subject 202. The patterned substrates are used to produce three-dimensional (3D) models of the subject 202 in the systems 1000 (FIG. 10A), 1020 (FIG. 10B), or 1040 (FIG. 10C) in accordance with some embodiments. In some embodiments, one or more projectors (e.g., projectors 1012-1 and 1012-2 in FIG. 10C) are used to illuminate the subject 202 with one or more light patterns instead of the patterned substrate 211.

The camera 204 includes a lens 218 to focus light onto the photodetector 216. In some embodiments the lens 218 is a zoom lens that provides variable heightened image resolution. The zoom lens may be motorized and controlled by associated control circuitry (e.g., included in the control circuitry 214) or may be manually adjustable. The high resolution provided by a zoom lens enables accurate measurement of imaged skin features (e.g., pore size, hair strands, hair follicles, spots, and moles). In some embodiments, a filter 209 is mounted in front of the lens 218 to filter out red light from the light received by the photodetector, instead of being mounted in line with a light source 208 and polarizer 210.

An adjustable polarizer 220 is rotatably mounted on the lens 218 and thereby coupled to the photodetector. In some embodiments, the polarizer 220 is an elliptical polarizer, or a circular polarizer, or a linear polarizer. Rotating the polarizer 220 provides an adjustable axis of polarization (also called herein the degree of polarization) of light received by the photodetector 216. In some embodiments, a motor 222 attached to the polarizer 220 rotates the polarizer 220 (e.g., in defined angular increments) in response to instructions from polarizer control circuitry on a control board 224 coupled to the motor 222 via one or more signal lines 238. In some embodiments, the control board 224 or equivalent control circuitry is integrated into the motor 222 or camera control circuitry 214. Alternatively, a knob 242 allows manual adjustment of a degree of rotation of the polarizer 220, as illustrated for the imaging apparatus 241 of the imaging system 240 (FIG. 2B) in accordance with some embodiments.

The polarizer 220 may be adjusted such that it is aligned with the polarizers 210 and thus admits light with the same polarization as light from the light sources 208 as filtered by the polarizers 210 while rejecting light with polarization perpendicular to the polarization of light from the sources 208 as filtered by the polarizers 210. In this configuration, the polarizer 220 is said to have 0° rotation with respect to the polarizers 210. With the polarizer 220 in this configuration, the photodetector 216 may acquire an image of the subject 202 corresponding to light reflected from the surface of the subject's skin 203.

The polarizer 220 may be adjusted such that it is rotated 90° with respect to the polarizers 210. In this configuration, the polarizer 220 rejects light with the polarization provided by the polarizers 210 and admits light having a perpendicular polarization. With the polarizer 220 in this configuration, the photodetector 216 may acquire a sub-surface skin image of the subject 202 (e.g., corresponding to light reflected from a depth beneath the surface of the subject's skin 203 that varies from approximately 350 microns for very dark skin to approximately 3 mm for very fair skin). With the polarizer 220 in this configuration and filters 209 being used to filter red light, the sub-surface skin image of the subject 202 corresponds to light reflected from a depth of 2 mm or more beneath the surface of the subject's skin 203 even for very dark skin.

Figure 9B:
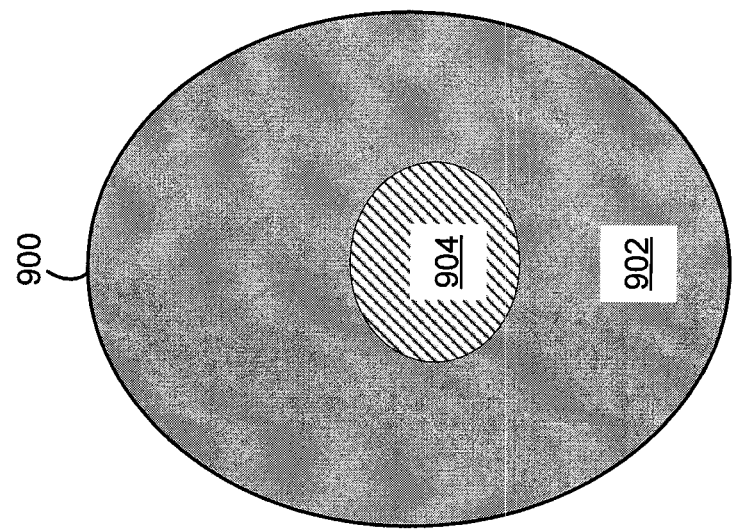
FIGS. 9A and 9B are schematic illustrations of images of the top of a subject's head in accordance with some embodiments.
Figure 9A:
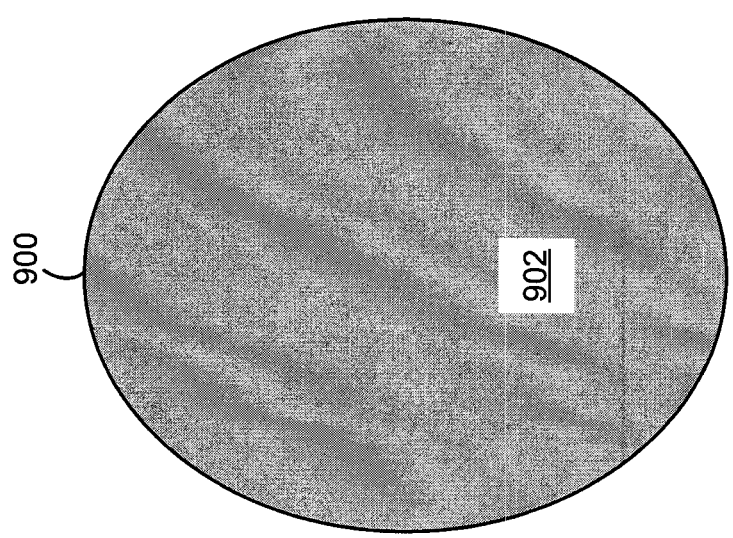

In some embodiments, the polarizer 220 is adjusted such that it is rotated 90° with respect to the polarizers 210 and the camera 204 is used to acquire an image of the hair 205 of the subject 202. The resulting image can reveal latent baldness or hair thinning that is not clearly visible to the naked eye or in images taken without a polarizer 220 or with the polarizer 220 aligned with the polarizers 210. FIG. 9A is a schematic illustration of the top of a subject's head 900 as seen by the naked eye or in images taken without a polarizer 220 or with the polarizer 220 aligned with the polarizers 210, in accordance with some embodiments. The subject appears to have an even head of hair 902, as indicated by the even shading in FIG. 9A, with no obvious balding or thinning of the hair 902 and thus little or no skin clearly visible beneath the hair 902. FIG. 9B is a schematic and prophetic illustration of an image of the top of the same head 900 taken by the camera 204 with the polarizer 220 rotated 90° with respect to the polarizers 210. In the image of FIG. 9B, a region 904 of latent balding is visible: in the region 904 of the image, skin is clearly visible beneath the hair, indicating thinning of the hair in the region 904. Such images can be used to provide early diagnosis of balding and allow the subject to begin treating regions 904 of latent balding with compounds for reducing hair loss (e.g., minoxidil).

The polarizer 220 may be adjusted such that it is rotated between 0° and 90° with respect to the polarizers 210. In this configuration, the polarizer 220 admits partially polarized light in accordance with Equation (1). With the polarizer 220 in this configuration, the photodetector 216 may acquire an image of the subject 202 corresponding to a combination of surface and sub-surface skin images. This image may be processed to produce a sub-surface skin image by subtracting an image taken with 0° rotation of the polarizer 220.

It should be noted that certain light sources (e.g., a laser and/or LED) emit polarized light and do not require separate polarizers 210. Thus, although the rotation of the polarizer 220 (and/or the axis of the polarizer 220) is described herein with respect to the polarizers 210, the rotation of the polarizer 220 (and/or the axis of the polarizer 220) can be determined with respect to the polarization of light emitted by the light sources 208 or the polarization of light impinging on the subject 202. For example, in some embodiments, the polarizer 220 is said to have 0° rotation (or a parallel polarization) when the polarizer 220 is aligned with the polarization of light emitted by the light sources 208 and thus admits light with the same polarization as light from the light sources 208. In some embodiments, the polarizer 220 is said to have 90° rotation (or a cross polarization) when the polarization of the polarizer 220 is substantially perpendicular to the polarization of light emitted by the light sources 208 and thus rejects light with the same polarization as light from the light sources 208.

In some embodiments, an imaging system includes a light shield 252 to shield the subject 202 from ambient light, as illustrated for the imaging system 250 (FIG. 2C) in accordance with some embodiments. In the system 250, the camera 204 is mounted on a back wall of the light shield 252, which extends outward from the camera housing 208 with a frustoconical shape. By shielding the subject 202 from ambient light, the light shield ensures that most of the light reflected from the subject 202 and received at the photodetector 216 originated from the light sources 208 and was filtered by the polarizers 210.

A computer 226 (FIGS. 2A-2B) is coupled to the camera 204 and control board 224 via one or more signal lines 236. The computer 226 includes memory 228 and one or more processors 230 as well as a monitor 232 for displaying a user interface (UI) 234. The UI 234 displays acquired and/or processed images as well as data calculated from acquired and/or processed images. In some embodiments, the computer 226 provides instructions to the control board 224 to rotate the polarizer 220, instructions to the camera 204 to adjust the zoom lens 218, and instructions to the camera 204 to acquire an image (i.e., to take a picture). The computer 800 (FIG. 8, below) illustrates an example of an implementation of the computer 226 in accordance with some embodiments.

In some embodiments, the functionality of the computer 226 and the control board 224 is integrated into the camera 204. In some embodiments, the camera 204 includes a display for viewing acquired and/or processed images as well as data calculated from acquired and/or processed images.

In some embodiments, the light sources 208, polarizers 210, and camera 204 (including polarizer 220) are mounted in an imaging box 302, as illustrated for the imaging system 300 (FIG. 3). The filters 209 and patterned substrate 211 also are optionally mounted in the imaging box 302. The imaging box 302, shown as mounted on a cart 310 for mobility, serves as a light shield (e.g., light shield 252, FIG. 2C) to shield the subject from ambient light. First and second light sources 208-1, 208-2 and first and second polarizers 210-1, 210-2 are mounted on a rear wall of the box 302, opposite from a chin rest 306 and forehead pad 304 for receiving the subject's head. An example of such an imaging box 302 is the Facial Stage DM-3 commercially available from Moritex Corporation of Tokyo, Japan. The system 300 also includes a printer 308 for printing acquired and/or processed images as well as data calculated from acquired and/or processed images.

In some embodiments, a reference material is included in acquired images to measure light source intensity output change and color change over time (e.g., resulting from drift in a light source 208). For example, a standard color chart such as the GretagMacbeth ColorChecker is placed in the field of imaging (e.g., beneath the chin of the subject 202) and used to calibrate the photodetector 216 and/or to post-process acquired images to adjust pixel values based on comparison to known pixel values for colors in the color chart. Furthermore, image processing software may be used to correct for optical aberrations.

In some imaging systems, multiple imaging apparatuses are positioned at different angles with respect to a subject to record images (e.g., surface or sub-surface skin images) of the subject from the different angles. The images are then processed to create a single three-dimensional model of the subject for display. Alternatively, a single imaging apparatus (e.g., apparatus 201, FIG. 2A, or 241, FIG. 2B) is successively positioned at different angles with respect to a subject to record successive images (e.g., surface or sub-surface skin images) of the subject from the different angles, which are then processed to create a single three-dimensional model of the subject for display.

Figure 2B:
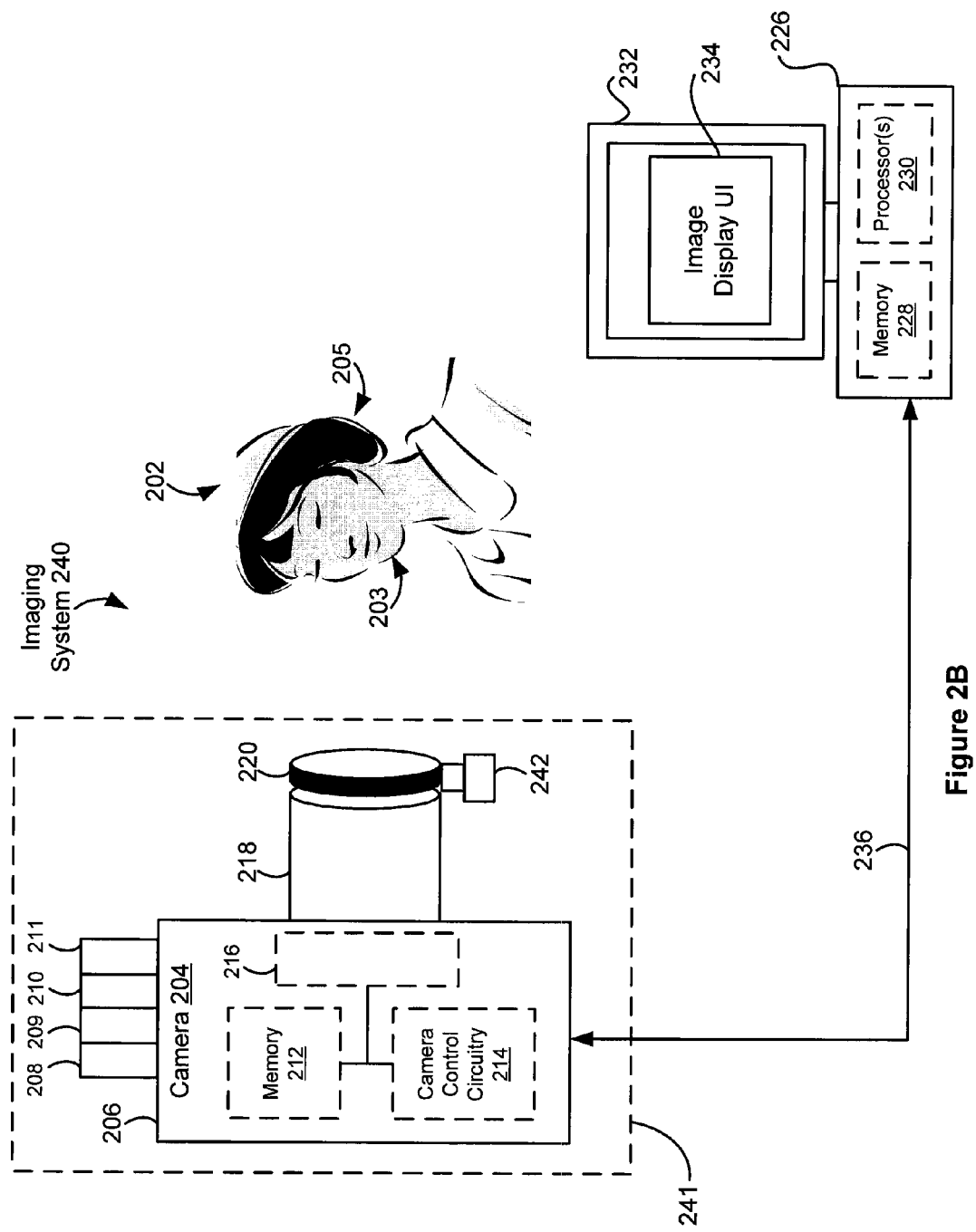
Figure 10A:
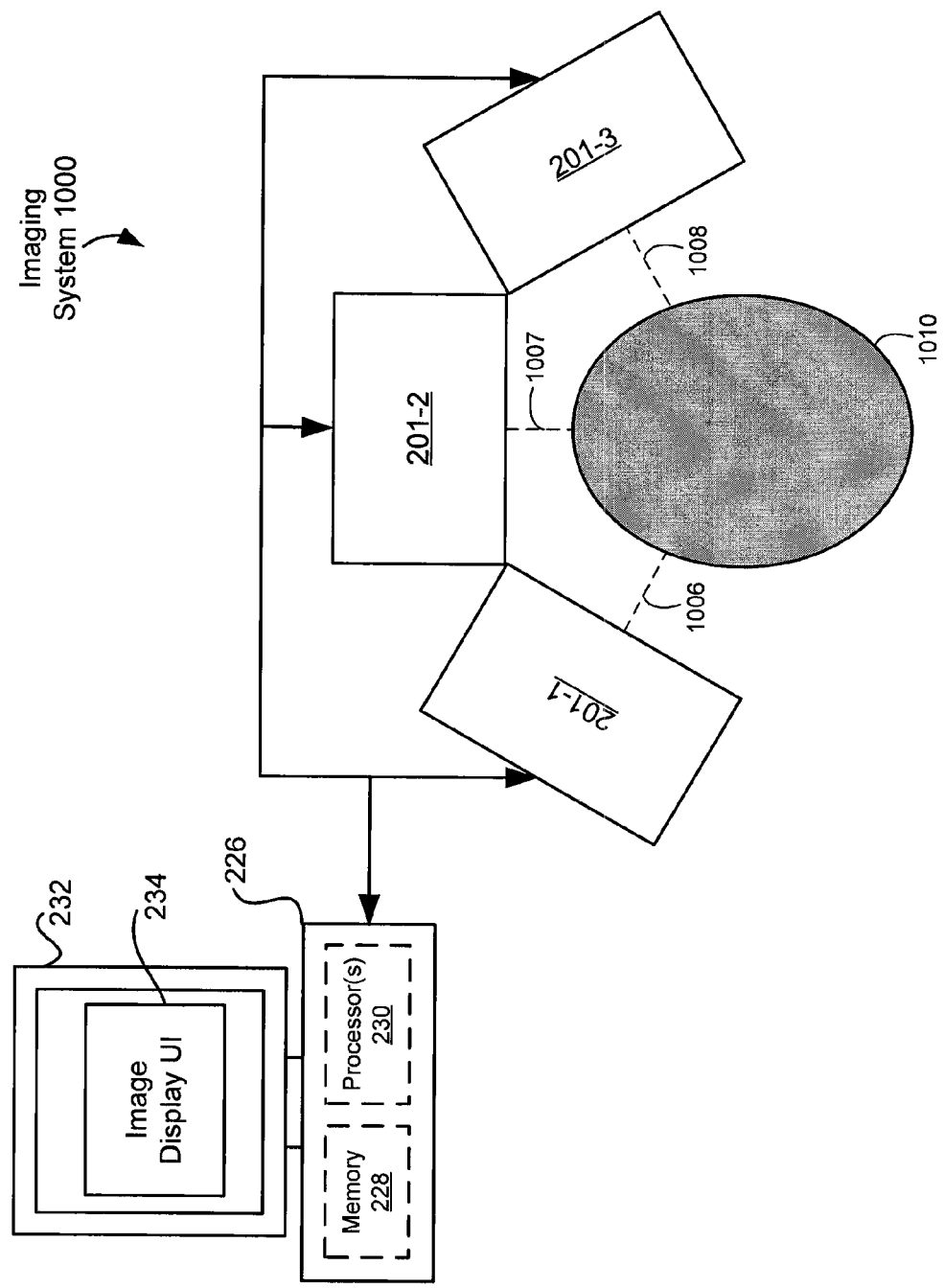

FIG. 10A illustrates an imaging system 1000 in which three imaging apparatuses 201-1, 201-2, and 201-3 are positioned to record respective images of a subject's head 1010 from respective angles, in accordance with some embodiments. Each of the apparatuses 201-1, 201-2, and 201-3 is an example of an imaging apparatus 201 (FIG. 2A). Alternatively, the imaging system 1000 includes three imaging apparatuses 241 (FIG. 2B). Typically, the subject's forehead is positioned against a forehead pad and/or a chin rest (e.g., the forehead pad and chin rest 1002 in FIG. 10B).

In FIG. 10A, the apparatus 201-2 is positioned directly in front of the subject's face and thus can acquire a frontal image of the subject's face, as indicated by the axis 1007 between the apparatus 201-2 and the subject. The apparatus 201-1 is positioned to acquire an image of the left side of the subject's face, as indicated by the axis 1006 between the apparatus 201-1 and the subject, and the apparatus 201-3 is positioned to acquire an image of the right side of the subject's face, as indicted by the axis 1008 between the apparatus 201-3 and the subject. The axis 1006 between the apparatus 201-1 and the subject (e.g., between the lens 218 of the camera 204 (FIGS. 2A-2C) in the apparatus 201-1 and the subject) intersects the subject's head 1010 on the left sidle of the subject face, indicating that the apparatus 201-1 is positioned to acquire an image of the left side of the subject's face. The axis 1008 between the apparatus 201-3 and the subject (e.g., between the lens 218 of the camera 204 (FIGS. 2A-2C) in the apparatus 201-3 and the subject) intersects the subject's head 1010 on the right side of the subject face, indicating that the apparatus 201-3 is positioned to acquire an image of the right side of the subject's face. Specifically, to acquire the image of the left side of the subject's face, the apparatus 201-1 is positioned with a specified angle (e.g., a right angle, or an acute angle) between the axes 1006 and 1007. Similarly, to acquire the image of the right side of the subject's face, the apparatus 201-3 is positioned with a specified angle (e.g., a right angle, or an acute angle) between the axes 1007 and 1008. For example, the apparatuses 201-1, 201-2, and 201-3 are positioned such that the angle between the axes 1006 and 1007, and also between the axes 1007 and 1008, is 45°, 60°, or 90°. Each of the three apparatuses 201-1, 201-2, and 201-3 is connected to the computer 226, which provides instructions to the three apparatuses 201-1, 201-2, and 201-3 to adjust their respective polarizers 220 (FIG. 2A) and to acquire respective images of the subject's head 1010, and which receives the acquired images for processing to generate a 3D model of the front and sides of the patient's head 1010 and thus of the patient's face.

FIG. 10B illustrates an imaging system 1020 in which five imaging apparatuses 201-1, 201-2, 201-3, 201-4, and 201-5 are positioned to record respective images of a subject's head 1010 from respective angles that correspond to respective sides of the subject's head 1010 and the top of the subject's head 1010, in accordance with some embodiments. Specifically, the apparatus 201-2 is positioned directly in front of the subject's face to acquire a frontal image of the subject's face. The apparatus 201-1 is positioned on the left side of the subject's head 1010 to acquire an image of the left side of the subject's head 1010, and the apparatus 201-3 is positioned on the right side of the subject's head 1010 to acquire an image of the right side of the subject's head 1010. The apparatus 201-4 is positioned directly behind the subject's head 1010 to acquire an image of the back side of the subject's head 1010, and the apparatus 201-5 is positioned directly above the subject's head 1010 to acquire an image of the top of the subject's head 1010. The apparatuses 201-1 through 201-4 are positioned, for example, at 90° increments about the subject's head 1010. Each of the five apparatuses 201-1 through 201-5 is connected to the computer 226, which provides instructions to the five apparatuses 201-1 through 201-5 to adjust their respective polarizers 220 (FIG. 2A) and to acquire respective images of the subject's head 1010, and which receives the acquired images for processing to generate a full three-dimensional model of the subject's head 1010. When displayed, this full three-dimensional model can be rotated 360° degrees around a vertical axis and 180° round a horizontal axis to provide views of the patient's head 1010 from any angle, such that any portion of the patient's head 1010 can be viewed. In FIG. 10B, the subject's forehead is positioned against a forehead pad and chin rest 1002.

Figure 10C:
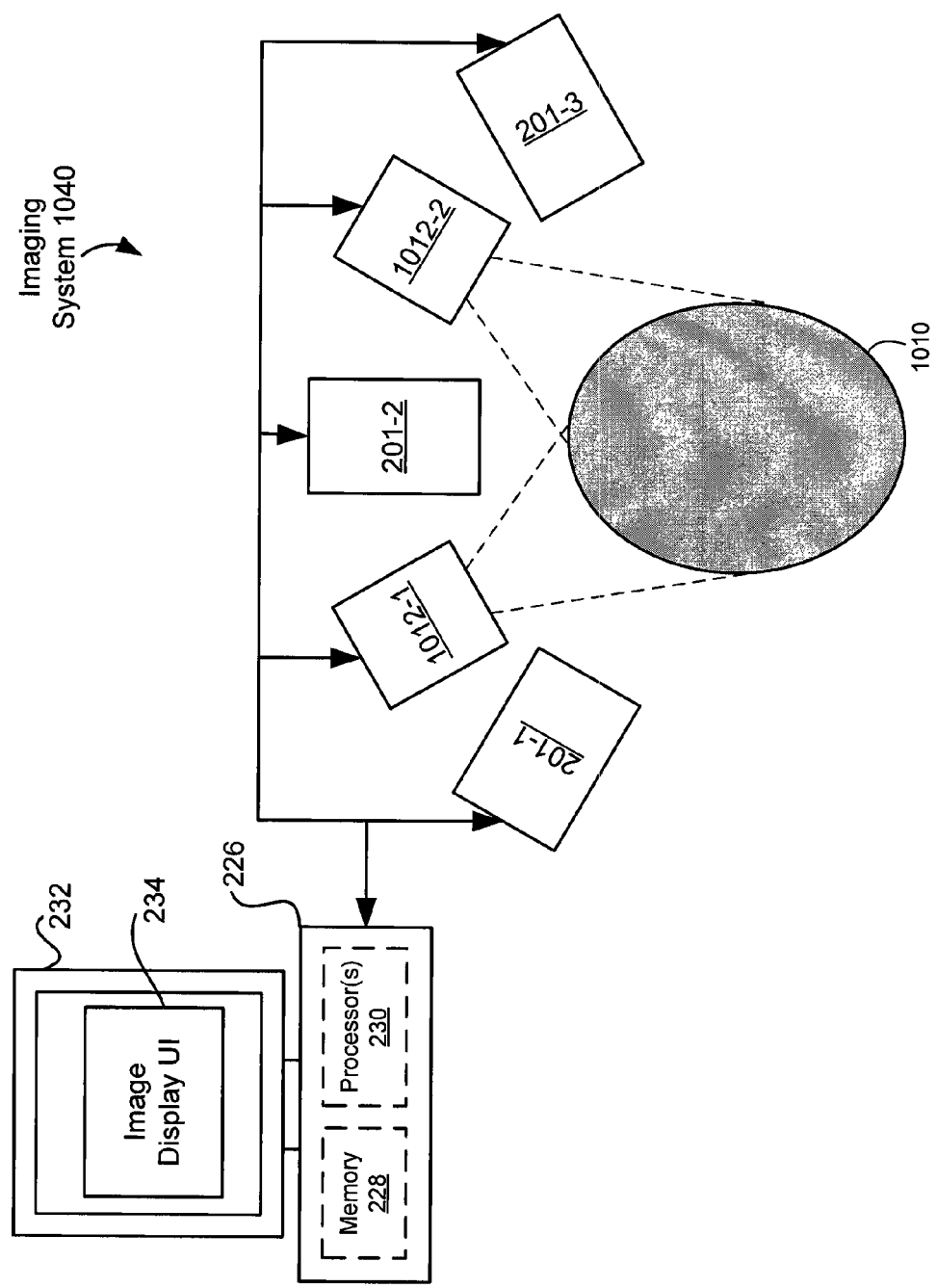

FIG. 10C illustrates an imaging system 1040, which is similar to the imaging system 1000 shown in FIG. 10A. The imaging system 1040 includes two projectors 1012-1 and 1012-2 positioned to illuminate respective portions of the subject's head 1010 from respective angles, in accordance with some embodiments. In some embodiments, each of the projectors 1012-1 and 1012-2 is positioned between two imaging apparatuses. In FIG. 10C, the projector 1012-1 is located between the imaging apparatuses 201-1 and 201-2, and the projector 1012-2 is located between the imaging apparatuses 201-2 and 201-3.

In some embodiments, each of the projectors 1012-1 and 1012-2 projects one or more respective images or graphical patterns generated by the computer 226. For example, a respective graphical pattern may include a grid of dots of multiple colors (e.g., red, green, and blue). In some embodiments, each of the projectors 1012-1 and 1012-2 illuminates the subject's head 1010 at one time. In other words, when the projector 1012-1 illuminates the subject's head 1010, the projector 1012-2 does not illuminate the subject's head 1010, and vice versa. In some embodiments, both projectors 1012-1 and 1012-2 illuminate the subject's head 1010 simultaneously.

In some embodiments, when each projector illuminates the subject's head 1010, a plurality of imaging apparatuses acquire a respective set of multiple images of the subject's head. In some embodiments, each set of multiple images is acquired simultaneously. For example, when the projector 1012-1 illuminates the subject's head 1010, the imaging apparatuses 201-1 and 201-2 acquire images of the subject's head 1010, and when the projector 1012-2 illuminates the subject's head 1010, the imaging apparatuses 201-2 and 201-3 acquire images of the subject's head 1010. The multiple images in each set are used to build a three-dimensional model, or a portion thereof, of the subject's head 1010.

In some embodiments, the imaging apparatuses 201-1 through 201-3 (FIGS. 10A and 10C) or 201-1 through 201-5 (FIG. 10B) acquire sub-surface images of a subject's skin by adjusting their respective polarizers 220 such that they are rotated 90° with respect to their respective polarizers 210. Alternatively, a single imaging apparatus 201 is successively moved to the positions shown for the imaging apparatuses 201-1 through 201-3 (FIG. 10A) or 201-1 through 201-5 (FIG. 10B) to acquire successive sub-surface images of a subject's skin by adjusting its polarizer 220 such that it is rotated 90° with respect to its polarizer 210. The resulting images are provided to the computer 226, which processes them to generate the three-dimensional model of the subject's head 1010. In other embodiments, the imaging apparatuses 201-1 through 201-3 (FIGS. 10A and 10C) or 201-1 through 201-5 (FIG. 10B) acquire respective first images for which their respective polarizers 220 are aligned with their respective polarizers 210, acquire respective second images for which their respective polarizers 220 are rotated to a specified angle between 0° and 90° with respect to their respective polarizers 210, and provide the respective first and second images to the computer 226. Alternatively, a single imaging apparatus 201 is successively moved to the positions shown for the imaging apparatuses 201-1 through 201-3 (FIG. 10A) or 201-1 through 201-5 (FIG. 10B) and acquires respective first and second images at each position. Generally, using multiple imaging apparatuses 201 has a higher throughput than moving a single imaging apparatus 201, because multiple images can be taken simultaneously. In addition, using multiple imaging apparatuses 201 reduces or eliminates registration error (or positioning error) associated with the movement of the subject and/or the imaging apparatus(es).

In some embodiments, the computer 226 subtracts each respective first image from its respective second image (or subtracts each respective second image from its respective first image) and uses the images resulting from this subtraction to generate the three-dimensional model of the subject's head 1010. In some embodiments, the resulting three-dimensional model includes a sub-surface representation of the subject's skin.

In some embodiments, each imaging apparatus in the system 1000 (FIG. 10A), 1020 (FIG. 10B), or 1040 (FIG. 10C) includes only a subset of the components of the imaging apparatus 201. For example, each imaging apparatus includes a photodetector 216 and corresponding polarizer 220 (FIG. 2A), but does not include a dedicated light source 208 and corresponding polarizer 210. Instead, the system 1000, 1020, or 1040 may include a single light source and optionally a corresponding polarizer, the position (and/or orientation) of which can be adjusted to provide suitable lighting for each of the imaging apparatuses.

To generate the three-dimensional model of the subject's head 1010, the computer 226 performs a process of morphing a generic face based on the acquired images that includes generating a distance map from points in the images of the subject's head 1010 to image features, as described for example in C. Zhang et al., "3-D Face Structure Extraction and Recognition from Images using 3-D Morphing and Distance Mapping," IEEE Transactions on Image Processing, Vol. 11, No. 11, pp. 1249-59 (November 2002), which is hereby incorporated by reference herein in its entirety. In another example, a morphing process is used as described in V. Blanz et al., "A Morphable Model for the Synthesis of 3D Faces," SIGGRAPH 99, pp. 187-194 (1999), which is hereby incorporated by reference herein in its entirety. In some embodiments, the morphing and distance mapping process is enhanced by using structured light projected onto the subject. For example, the subject is illuminated through a patterned substrate 211, which results in the projection of structured light (e.g., a light grid or array of points of light) onto the subject. The structured light is used to identify points on the subject (e.g., on the subject's face) in the distance-mapping and morphing process.

Skin pixels in surface or sub-surface skin images (e.g., images generated using an imaging system 200, 240, 250, 300, 1000, or 1020, FIGS. 2A-2C, 3, and 10A-10C) may be analyzed to identify at least one skin condition by comparing pixel values to predetermined criteria associated with various skin conditions. Conditions associated with the skin that may be detected and classified include, but are not limited to, skin tone/color, pigment evenness, pigment darkness, diffuse redness (e.g., indicative of sensitive or reactive skin), intense localized red levels (e.g., indicative of vascular lesions/telangiectasias), radiance intensity, enlarged pores, roughness variation, emerging lines, fine lines, wrinkles, UV damage, pore health, hydration levels, collagen content, skin type, topical inflammation or recent ablation, keratosis, deeper inflammation, sun spots, different kinds of pigmentation including freckles, moles, growths, undereye circles, scars, acne, fungi, erythema and other artifacts. In addition, image pixels may be used to perform feature measurements, such as the size or volume of a lip, nose, eyes, ears, chin, cheeks, forehead, eyebrows, teeth, or other features. Other examples of feature measurements, including pore size measurements, spot counts, and measurement of the length, thickness and/or curvature of an eyelash, can be made based on information from image pixels. Image pixels may be used to characterize lip conditions, which may include, without limitation, lip surface area, color, fine lines, wrinkles, and characteristics associated with lip edge demarcation. Characteristics associated with lip edge demarcation may include, for example, color contrast, line roughness, and color variation.

In some embodiments, a skin condition look-up table 600 (FIG. 6A) is used to identify skin conditions. A color value and an intensity value is measured for a respective skin pixel or group of skin pixels and compared against color and intensity values for various skin conditions as stored in the table 600. The table 600 includes a row 602 for each respective skin condition stored in the table 600. Each row includes fields that specify a name 602 of a respective skin condition as well as the minimum color value 606, maximum color 608, minimum intensity value 610, and maximum intensity value 612 associated with the respective skin condition. If the measured color and intensity values match the values specified in a row 602, the respective skin condition corresponding to the row is identified.

In some embodiments, to analyze either skin pixels or non-skin pixels (e.g., pixels corresponding to hair, clothing, eyes, lips, etc.) in surface or sub-surface skin images, pixels are analyzed on a pixel-by-pixel basis to distinguish skin pixels from non-skin pixels. Identification of skin and non-skin pixels is described, for example, in U.S. Pat. No. 7,454,046, entitled "Method and System for Analyzing Skin Conditions Using Digital Images," issued Nov. 18, 2008, which is hereby incorporated by reference herein in its entirety. For example, assuming the pixels have red, green, and blue sub-pixels with pixel values that range between 0-255, pixels with red channel values in the range of 105-255, green channel values in the range of 52-191, and blue channel values in the range of 32-180 are identified as skin pixels. Furthermore, in some embodiments a pre-stored template or coordinate reference is used to define certain pixels as non-skin pixels and a skin map or skin mask may be used to define certain pixels as non-skin pixels, as described in U.S. Pat. No. 7,454,046 in accordance with some embodiments.

In some embodiments, a surface skin image is compared to a sub-surface skin image to compare surface and sub-surface skin conditions. For example, surface and sub-surface pigmentation may be compared.

In some embodiments, a sub-surface image is used alone to analyze pigmentation or other skin conditions. Sub-surface images exclude wrinkles on the surface of the skin, which can interfere with imaging of pigmentation. Sub-surface images also exclude glare from the surface of the skin, which also can interfere with imaging of pigmentation and other skin features or conditions. Accordingly, sub-surface images can provide a more accurate indication of skin tone or color than surface images, and can provide a more accurate indication of other skin conditions as well.

In some embodiments, images (either surface or sub-surface) generated by an imaging system (e.g., an imaging system 200, 240, 250, 300, 1000, 1020, or 1040, FIGS. 2A-2C, 3, and 10A-10C) are compared with old (i.e., historical) images stored in memory to identify variations in skin conditions and features over time. For example, a newly generated image may be displayed next to a stored historical image in a user interface (e.g., UI 234, FIGS. 2A-2B). A computer system (e.g., the computer 226, FIGS. 2A-2B) performs automated comparison of one or more newly generated images with one or more historical images to track changes in skin conditions and features. For example, the system calculates changes in pigmentation (e.g., skin tone) and changes in size or color of features on the skin. Results of this automated comparison are displayed in a user interface (e.g., UI 234, FIGS. 2A-2B).

When comparing multiple images, the images are first aligned to allow the same features to be identified in the multiple images. In some embodiments, images are aligned using a three-point selection process that identifies points in the center of the eyes and the center of the lips and aligns the images accordingly.

Figure 4:
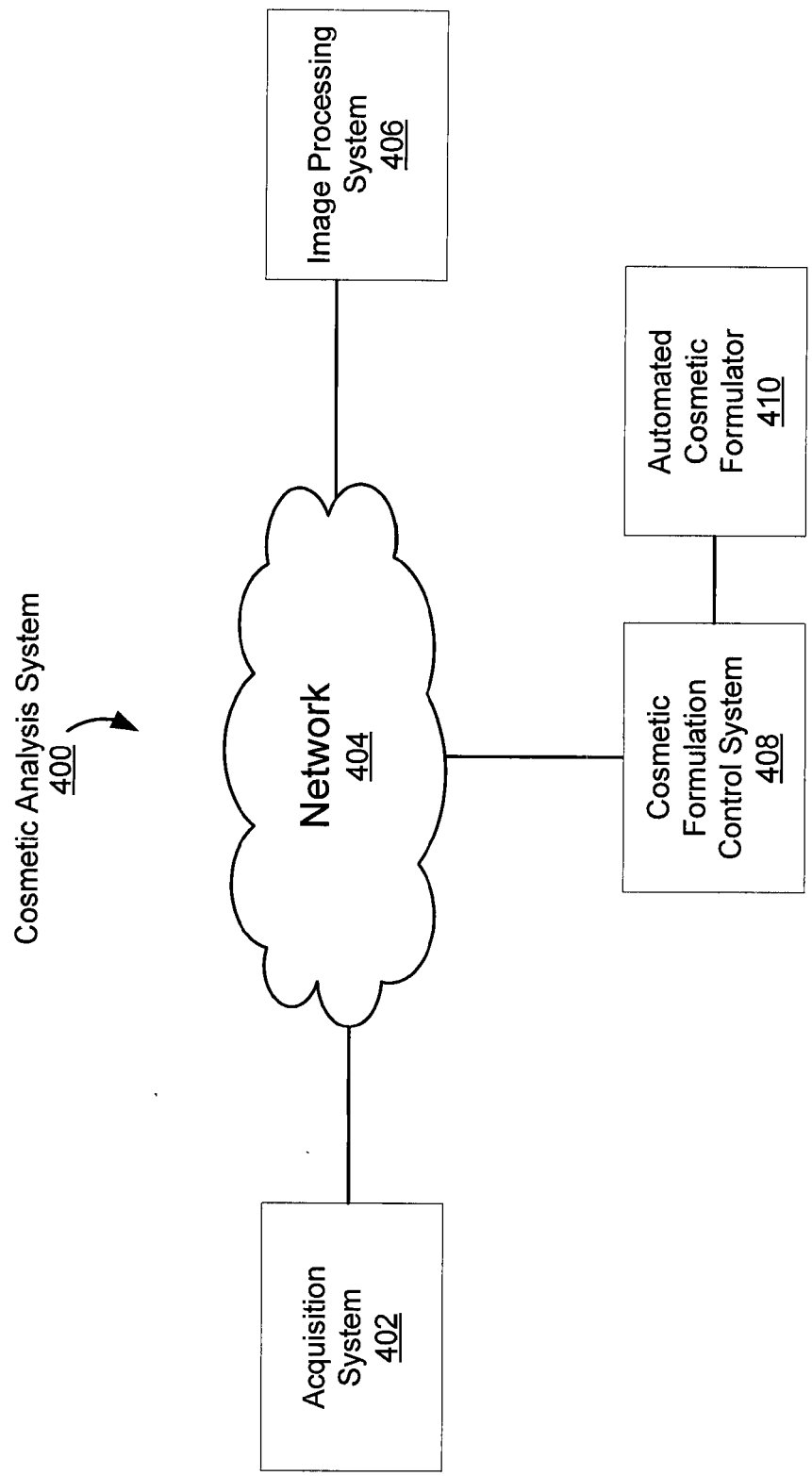
FIG. 4 is a block diagram illustrating a system in which a network couples an acquisition system to an image processing system and a cosmetic formulation system in accordance with some embodiments.

In the imaging systems 200, 240, 300, 1000, 1020, and 1040 (FIGS. 2A-2B, 3, and 10A-10C) the computer 226 is directly connected to the camera(s) 204. In some embodiments, however, an acquisition system 402 that includes one or more cameras 204 is coupled to an image processing system 406 through a network 404. FIG. 4 is a block diagram illustrating a system 400 in which a network 404 couples an acquisition system 402 to an image processing system 406 in accordance with some embodiments. The acquisition system 402 includes, for example, one or more imaging apparatuses 201 (FIG. 2A) or 241 (FIG. 2B). The network 404 may be any suitable wired and/or wireless network and may include a local area network (LAN), wide area network (WAN), virtual private network (VPN), the Internet, metropolitan area network (MAN), or any combination of such networks. The image processing system 406 may perform various types of processing related to images acquired by the acquisition system, including without limitation subtracting a first image from a second image to generate a sub-surface image, analyzing pixel data to identify skin or feature conditions, comparing images, and generating a three-dimensional model.

In some embodiments, a system such as the computer 226 (FIG. 2A-2B) or image processing system 406 (FIG. 4) generates a recommendation for a cosmetic product based on analysis of skin pixels. For example, the system may analyze skin color in a sub-surface image and recommend a cosmetic product based on the skin color. In some embodiments, the recommendation is displayed to the subject 202 (e.g., in the UI 234, FIGS. 2A-2B) or printed out (e.g., using the printer 308, FIG. 3). In some embodiments, the recommendation is provided at the point of sale (POS) where the subject may buy the recommended product or is displayed on a web page that the subject may use to order the recommended product.

In some embodiments, the image processing system 406 (or alternatively the acquisition system 402) transmits the recommendation (e.g., through the network 404) to a cosmetic formulation control system 408 coupled to an automated cosmetic formulator 410. The formulator 410 then prepares the recommended product in real time, thus providing the subject with a customized cosmetic product based on the recommendation.

In some embodiments, the image processing system 406 and cosmetic formulation control system 408 are integrated into a single system.

Figure 5:
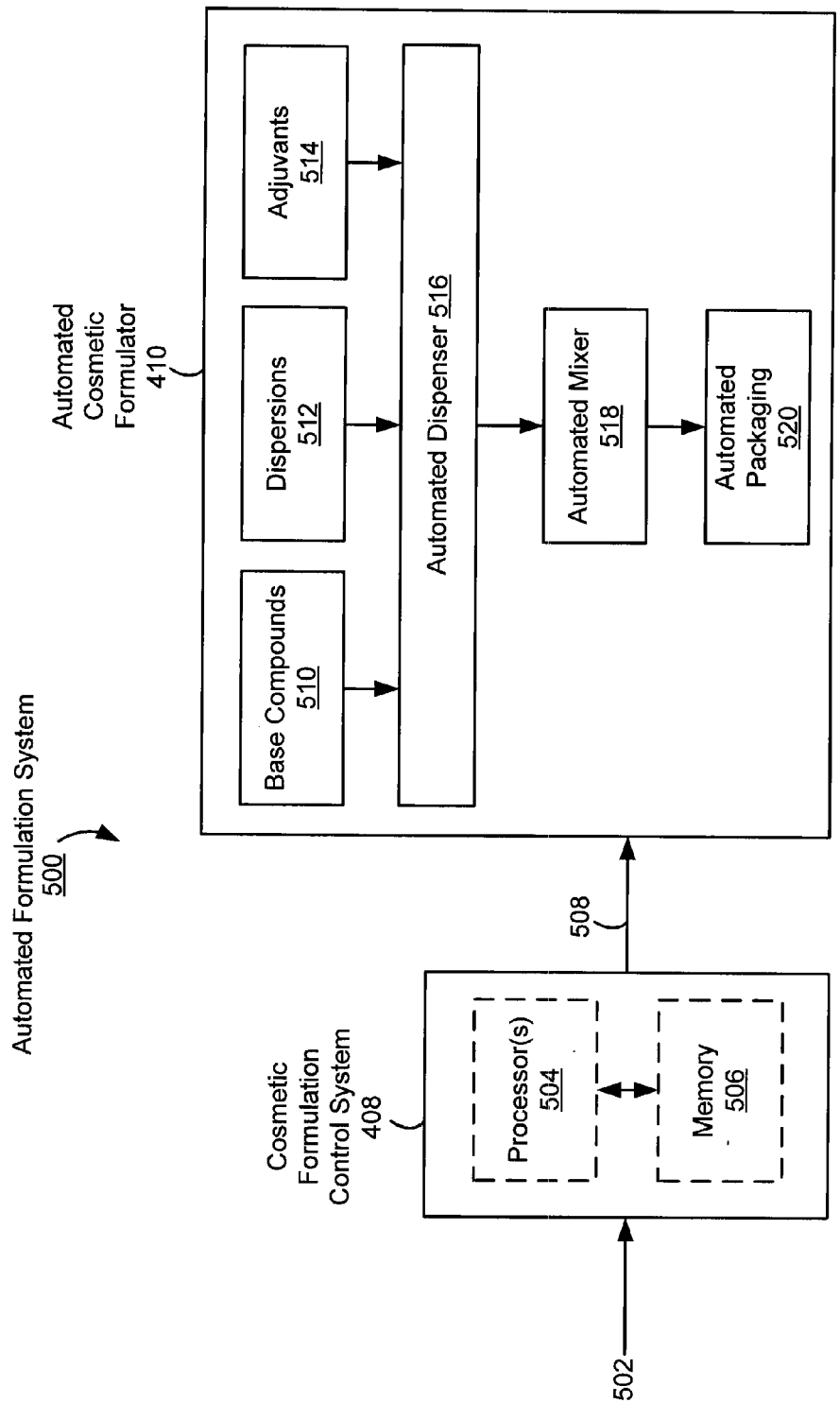
FIG. 5 is a block diagram illustrating an automated formulation system that includes a cosmetic formulation control system coupled to an automated cosmetic formulator in accordance with some embodiments.

FIG. 5 is a block diagram illustrating an automated formulation system 500 that includes a cosmetic formulation control system 408 coupled to an automated cosmetic formulator 410 in accordance with some embodiments. The control system 408, which includes memory 506 and one or more processors 504, receives a recommendation for a customized cosmetic product through a network connection 502. Based on the recommendation, the control system 408 determines a formula for the customized cosmetic product (e.g., using a look-up table stored in the memory 506) and provides instructions to the automated cosmetic formulator 410 via one or more signal lines 508 to mix the customized cosmetic product. Alternatively, the formula is provided to the system 500 in the recommendation. An automated dispenser 516 in the formulator 410 dispenses one or more base compounds 510, dispersions 512, and adjuvants 514 to an automated mixer 518 in accordance with the formula. The mixer 518 mixes the base compounds 510, dispersions 512, and adjuvants 514 and provides the mixture to an automated packaging unit 520, which packages the mixture and dispenses it. In some embodiments, the system 500 is located at the POS. Alternatively, the customized cosmetic product provided by the system 500 may be shipped to the customer.

FIG. 6B is a diagram illustrating a data structure of a cosmetic product recommendation table 630 used to generate a recommendation for a cosmetic product based on analysis of skin pixels. A color value and an intensity value is measured for a respective skin pixel or group of skin pixels and compared against color and intensity values for various cosmetic products as stored in the table 630. The table 630 includes a row 632 for each respective cosmetic product stored in the table 630. Each row 632 includes fields that specify a respective cosmetic product 634 as well as the minimum color value 636, maximum color 638, minimum intensity value 640, and maximum intensity value 642 associated with the respective skin condition. If the measured color and intensity values match the values specified in a row 632, the respective cosmetic product corresponding to the row is recommended.

Figure 7A:
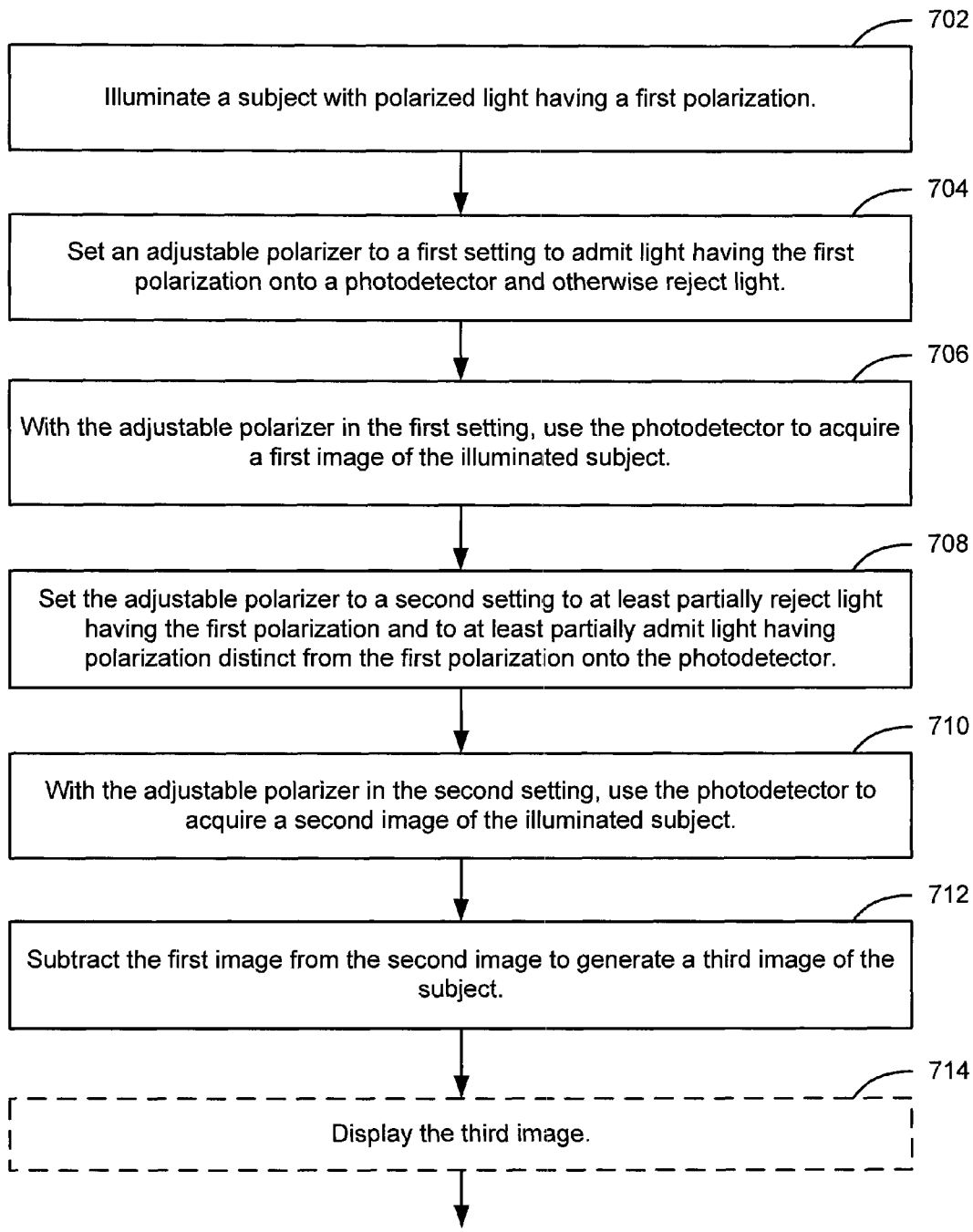
FIGS. 7A-7C are flow diagrams illustrating a method of generating a sub-surface skin image in accordance with some embodiments.

FIG. 7A is a flow diagram illustrating a method 700 of generating a sub-surface skin image in accordance with some embodiments. The method 700 is performed, for example, in the imaging system 200, 240, 300, 1000, 1020, or 1040 (FIGS. 2A-2B, 3, and 10A-10C). In the method 700, a subject is illuminated (702) with polarized light having a first polarization. For example, the subject 202 (FIGS. 2A-2C) is illuminated using light from one or more light sources 208 as filtered by one or more polarizers 210.

An adjustable polarizer (e.g., polarizer 220, FIGS. 2A-2C) is set (704) to a first setting (e.g., a 0° rotation with respect to the polarizers 210) to admit light having the first polarization onto a photodetector (e.g., photodetector 216, FIGS. 2A-2C) and otherwise reject light. With the adjustable polarizer in the first setting, the photodetector is used (706) to acquire a first image of the illuminated subject. The first image thus corresponds to light reflected from the surface of the subject's skin.

The adjustable polarizer is set (708) to a second setting to at least partially reject light having the first polarization and to at least partially admit light having polarization distinct from the first polarization onto the photodetector. The second setting thus corresponds to a degree of rotation greater that 0° with respect to the polarizers 210. With the adjustable polarizer in the second setting, the photodetector is used (710) to acquire a second image of the illuminated subject. The second image thus at least partially includes sub-surface image data.

The first image is subtracted (712) from the second image to generate a third image of the subject. This subtraction is performed, for example, by the computer 226 (FIGS. 2A-2B, 3, and 10A-10C) or by the image processing system 406 (FIG. 4). Because the first image is a surface image and the second image at least partially includes sub-surface image data, subtracting the first image from the second image produces a sub-surface image. The third image thus is a sub-surface image of the subject's skin. In some embodiments, if the second setting completely rejects light having the first polarization, the subtraction operation 712 is omitted, since the second image already is a sub-surface image.

In some embodiments, the third image is displayed (714) (e.g., in the UI 234, FIGS. 2A-2B). In some embodiments, the third image is analyzed and results of the analysis are displayed (e.g., in the UI 234, FIGS. 2A-2B).

Figure 2C:
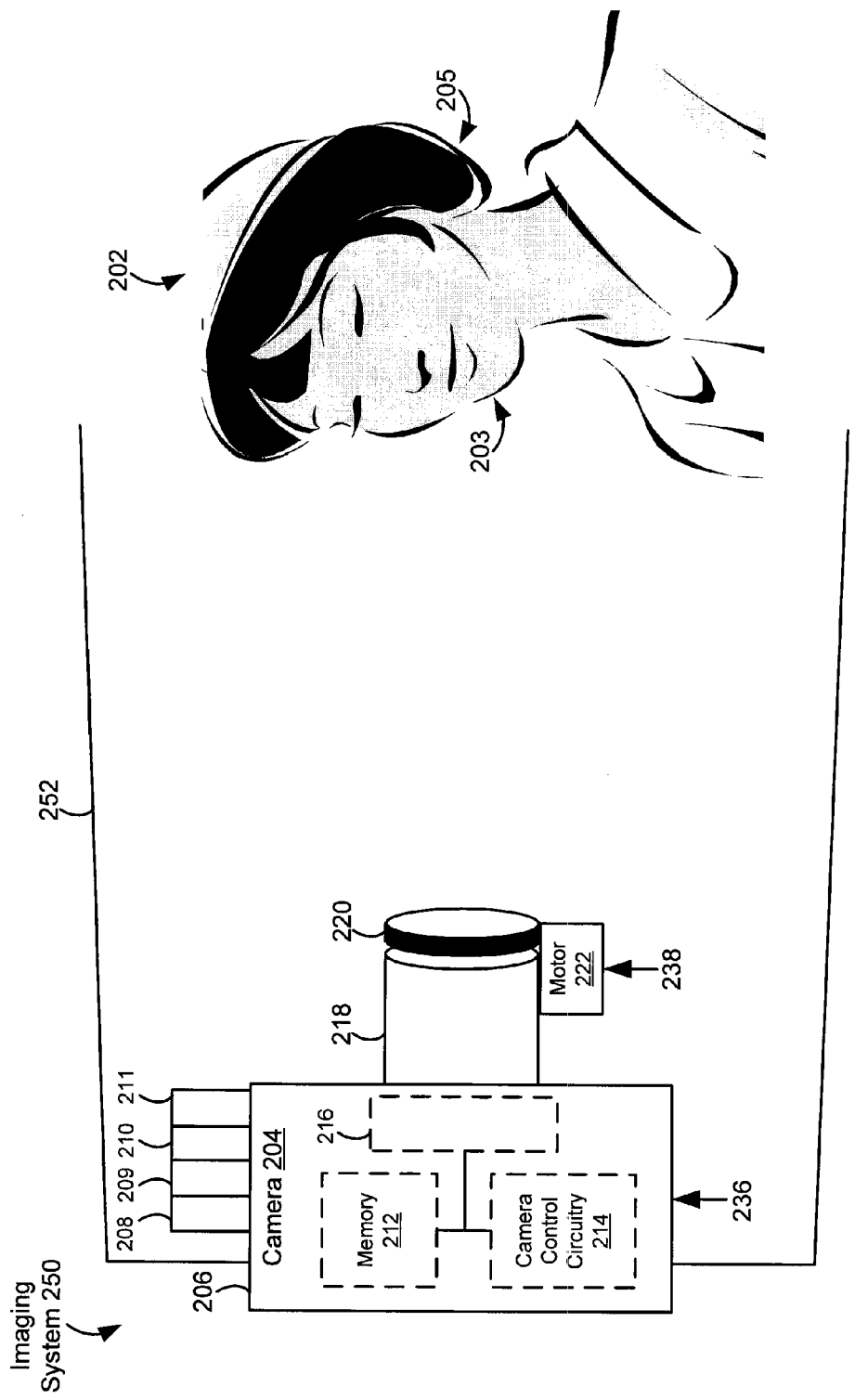

In some embodiments, the method 700 includes filtering red light from the light illuminating the subject or the light admitted onto the photodetector (e.g., using filters 209 (FIGS. 2A-2C).

In some embodiments, the operations 702-712 are repeated multiple times to generate a plurality of third images of the subject from different angles, as described for example with regard to FIGS. 10A-10C. The plurality of third images are processed (e.g., by performing three-dimensional morphing and distance mapping) to generate a three-dimensional model of the subject for display.

Figure 7B:
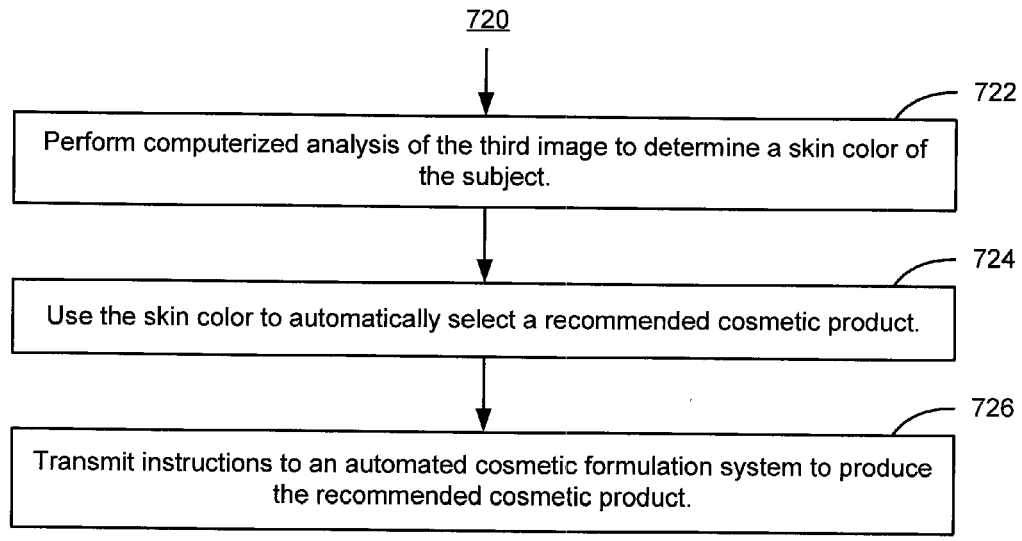

In some embodiments, the method 700 further includes a method 720 as illustrated in FIG. 7B in accordance with some embodiments. In the method 720, a computerized analysis is performed (722) of the third image to determine a skin color of the subject. The skin color is used to automatically select (724) a recommended cosmetic product. Instructions are transmitted (726) to an automated cosmetic formulation system (e.g., the system 500, FIG. 5) to produce the recommended cosmetic product. The method 720 is performed, for example, by the computer 226 (FIGS. 2A-2B, 3, and 10A-10C) or by the image processing system 406 (FIG. 4).

Figure 7C:
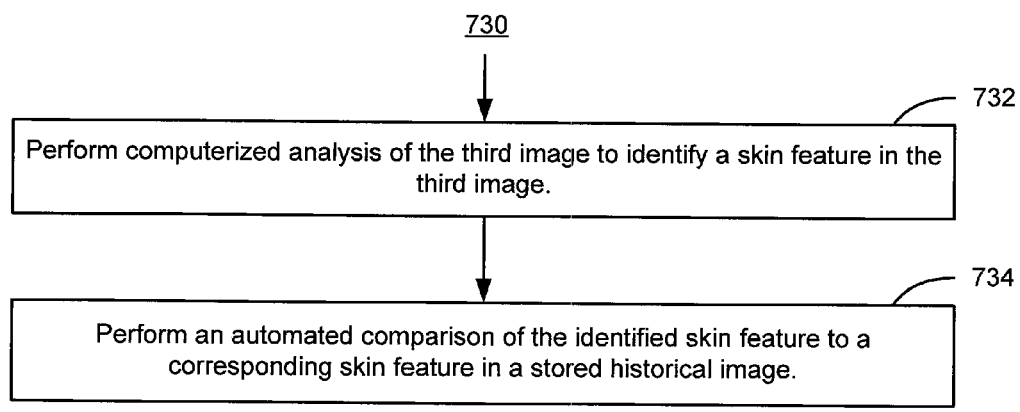

In some embodiments, the method 700 further includes a method 730 as illustrated in FIG. 7C in accordance with some embodiments. In the method 730, a computerized analysis of the third image is performed (732) to identify a skin feature (e.g., a skin condition) in the third image. An automated comparison of the identified skin feature to a corresponding skin feature in a stored historical image is performed (734). Results of the comparison are displayed (e.g., in the UI 234, FIGS. 2A-2B and 10A-10C). The method 730 is performed, for example, by the computer 226 (FIGS. 2A-2B and 10A-10C) or by the image processing system 406 (FIG. 4).

In some embodiments, the photodetector is calibrated (e.g., using a color chart positioned in the field of image) and the first and second images are corrected in accordance with the calibration.

FIG. 7D is a flow diagram illustrating a method 740 of processing and displaying images of skin in accordance with some embodiments. The method 740 is implemented at a computer system such as the computer 226 (FIGS. 2A-2B, 3, and 10A-10C) or the image processing system 406 (FIG. 4).

In the method 740, a first image of a subject (e.g., subject 202, FIGS. 2A-2C) is received (742). The first image was acquired at an imaging apparatus (e.g., 201 or 241, FIGS. 2A-2C) with the subject illuminated with light having a first polarization (e.g., light from one or more light sources 208 as filtered by one or more polarizers 210, FIGS. 2A-2C). The first image was acquired with the imaging apparatus configured to receive light having the first polarization and to otherwise reject light (e.g., an adjustable polarizer 220 was set to a 0° rotation with respect to the polarizers 210).

A second image of the subject is received (744). The second image was acquired at the imaging apparatus with the subject illuminated with light having the first polarization. The second image was acquired with the imaging apparatus configured to at least partially reject light having the first polarization and to at least partially receive light having polarization distinct from the first polarization (e.g., an adjustable polarizer 220 was set to a rotation of greater than 0° with respect to the polarizers 210).

The first image is subtracted (746) from the second image to generate a third image of the subject. The third image is displayed (748). In some embodiments, the third image is analyzed to identify skin conditions or features and results of the analysis are displayed.

Figure 7E:
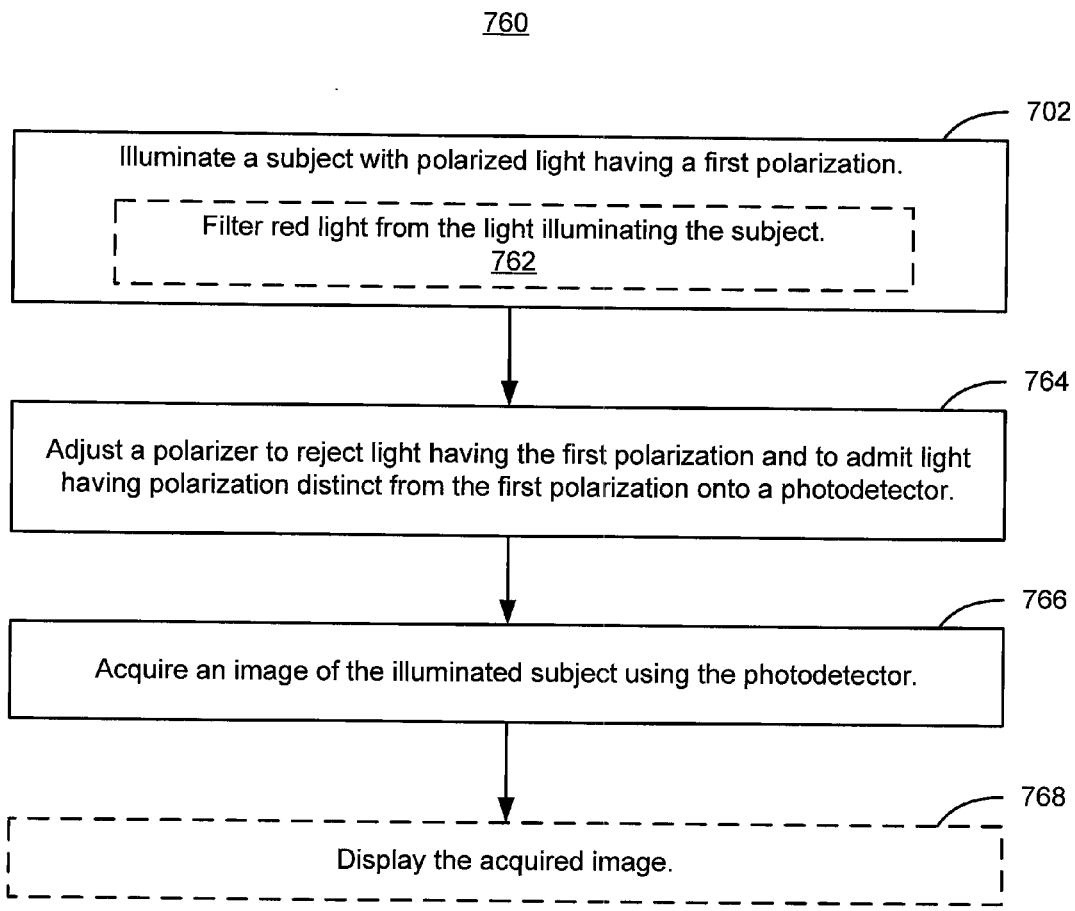
FIG. 7E is a flow diagram illustrating a method of imaging skin in accordance with some embodiments.

FIG. 7E is a flow diagram illustrating a method 760 of imaging skin in accordance with some embodiments. The method 760 is performed, for example, in the imaging system 200, 240, 300, 1000, 1020, or 1040 (FIGS. 2A-2B, 3, and 10A-10C). In the method 760, a subject (e.g., the subject 202, FIGS. 2A-2C) is illuminated (702) with polarized light having a first polarization, as described for the method 700 (FIG. 7A). In some embodiments, the illuminating (702) includes filtering (762) red light from the light illuminating the subject (e.g., using filters 209, FIGS. 2A-2C) or filtering red light from the light admitted onto a photodetector to be used to acquire an image of the illuminated subject.

A polarizer is adjusted (764) to reject light having the first polarization and to admit light having polarization distinct from the first polarization onto the photodetector. For example, the polarizer 220 (FIGS. 2A-2C) is adjusted to a setting with a 90° rotation with respect to the polarizers 210. With the polarizer in this setting, an image of the illuminated subject is acquired (766) using the photodetector (e.g., the photodetector 216, FIGS. 2A-2C).

In some embodiments, the illuminating (702) includes illuminating the subject's skin (e.g., the skin on the subject's face), and the image acquired in the operation 766 includes a sub-surface image of the patient's skin. In some embodiments, the illuminating (702) includes illuminating the subject's hair, and the image acquired in the operation 766 includes an image of the subject's hair and underlying skin (e.g., as shown in FIG. 9B); this image reveals the presence, if any, of latent balding.

In some embodiments, the acquired image is displayed (768) (e.g., in the UI 234, FIGS. 2A-2B). In some embodiments, the acquired image is analyzed and results of the analysis are displayed (e.g., in the UI 234, FIGS. 2A-2B).

Figure 8:
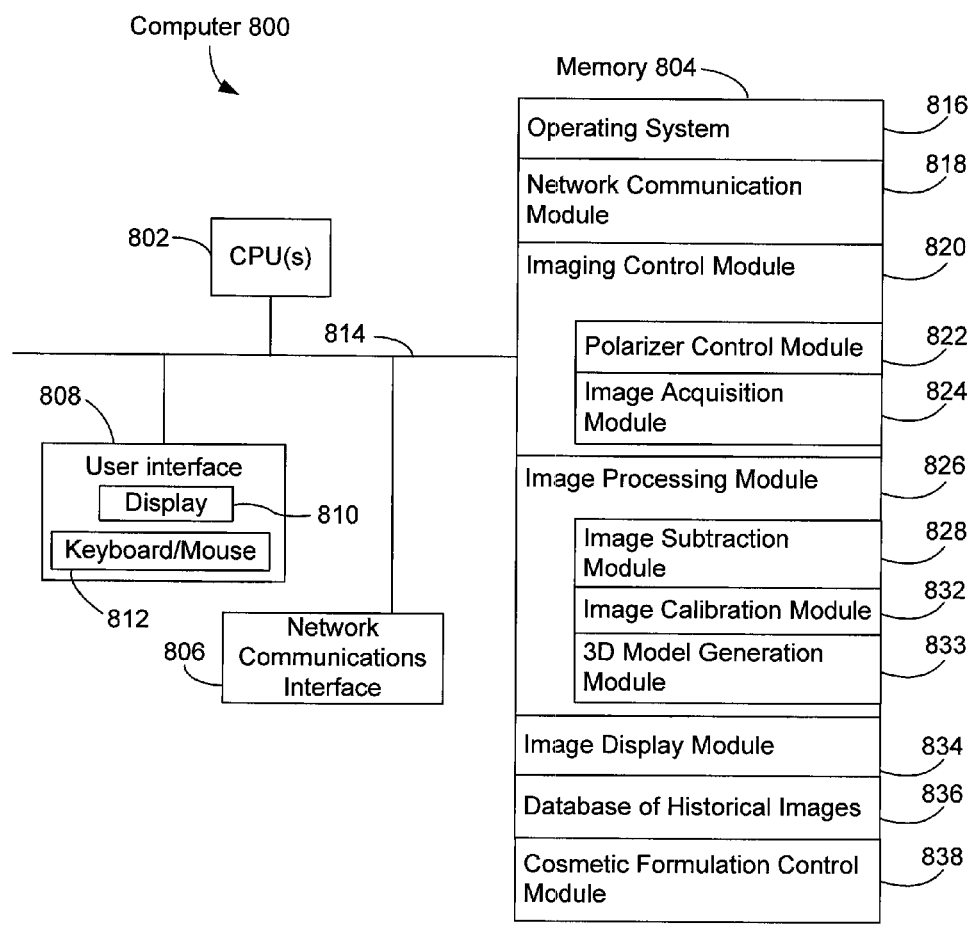
FIG. 8 is a block diagram illustrating a computer in accordance with some embodiments.

FIG. 8 is a block diagram illustrating a computer 800 in accordance with some embodiments. In some embodiments the computer 800 is an example of an implementation of the computer 226 (FIGS. 2A-2B, 3, and 10A-10C), image processing system 406 (FIG. 4), or cosmetic formulation control system 408 (FIG. 4). The computer 800 typically includes one or more central processing units (CPUs) 802, one or more network or other communications interfaces 806, memory 804, and one or more communication buses 814 for interconnecting these components. The communication buses 814 may include circuitry (sometimes called a chipset) that interconnects and controls communications between system components. The computer 800 may also include user interface hardware 808 comprising a display device 810 and a keyboard and/or mouse (or other pointing device) 812. Memory 804 includes high-speed random access memory, such as DRAM, SRAM, DDR RAM or other random access solid state memory devices; and may include non-volatile memory, such as one or more magnetic disk storage devices, optical disk storage devices, flash memory devices, or other non-volatile solid state storage devices. Memory 804 may optionally include one or more storage devices remotely located from the CPU(s) 802. Memory 804, or alternately non-volatile memory device(s) within memory 804, comprises a computer readable storage medium. In some embodiments, memory 804 stores instructions for performing all or a portion of the methods 700, 720, 730, 740, and/or 760 (FIGS. 7A-7E). In some embodiments, memory 804 stores the following programs, modules, and data structures, or a subset thereof:

an operating system 816 that includes procedures for handling various basic system services and for performing hardware dependent tasks;

a network communication module 818 that is used for connecting the computer 800 to other computers via the one or more communication network interfaces 806 and one or more communication networks, such as the Internet, other wide area networks, local area networks, metropolitan area networks, and so on;

an imaging control module 820 for controlling an imaging system (e.g., a system 200, 240, 250, 300, 402, 1000, 1020, or 1040, FIGS. 2A-2C, 3, 4, and 10A-10C);

an image processing module 826 to process acquired skin images (e.g., images acquired using a system 200, 240, 250, 300, 402, 1000, 1020, or 1040, FIGS. 2A-2C, 3, 4, and 10A-10C);

an image display module 834 module to display skin images and data corresponding to skin images;

a database of historical images 836 (e.g., for comparison to newly acquired images); and a cosmetic formulation control module 838 for controlling an automated cosmetic formulator (e.g., formulator 48, FIGS. 4 and 5).

In some embodiments, the imaging control module 820 includes a polarizer control module 822 for automatically controlling an adjustable polarizer (e.g., for controlling the motor 222 via the control board 224, FIG. 2A) and/or an image acquisition module 824 for controlling image acquisition (e.g., using a camera 204, FIGS. 2A-2C).

In some embodiments, the image processing module 826 includes an image subtraction module 828 for subtracting respective acquired images (e.g., in accordance with operations 712 (FIG. 7A), 746 (FIG. 7D) or 768 (FIG. 7E)), an image calibration module 832, and/or a three-dimensional model generation module 833 (e.g., for generating a three-dimensional model of a subject using images acquired by the imaging systems 1000, 1020, or 1040, FIGS. 10A-10C).

Each of the above identified elements in FIG. 8 may be stored in one or more of the previously mentioned memory devices. Each of the above-identified modules corresponds to a set of instructions for performing a function described above. These sets of instructions need not be implemented as separate software programs, procedures or modules. Various subsets of the above-identified modules may be combined or otherwise re-arranged in various embodiments. In some embodiments, memory 804 may store a subset of the modules and data structures identified above. Furthermore, memory 804 may store additional modules and data structures not described above.

Figure 11B:
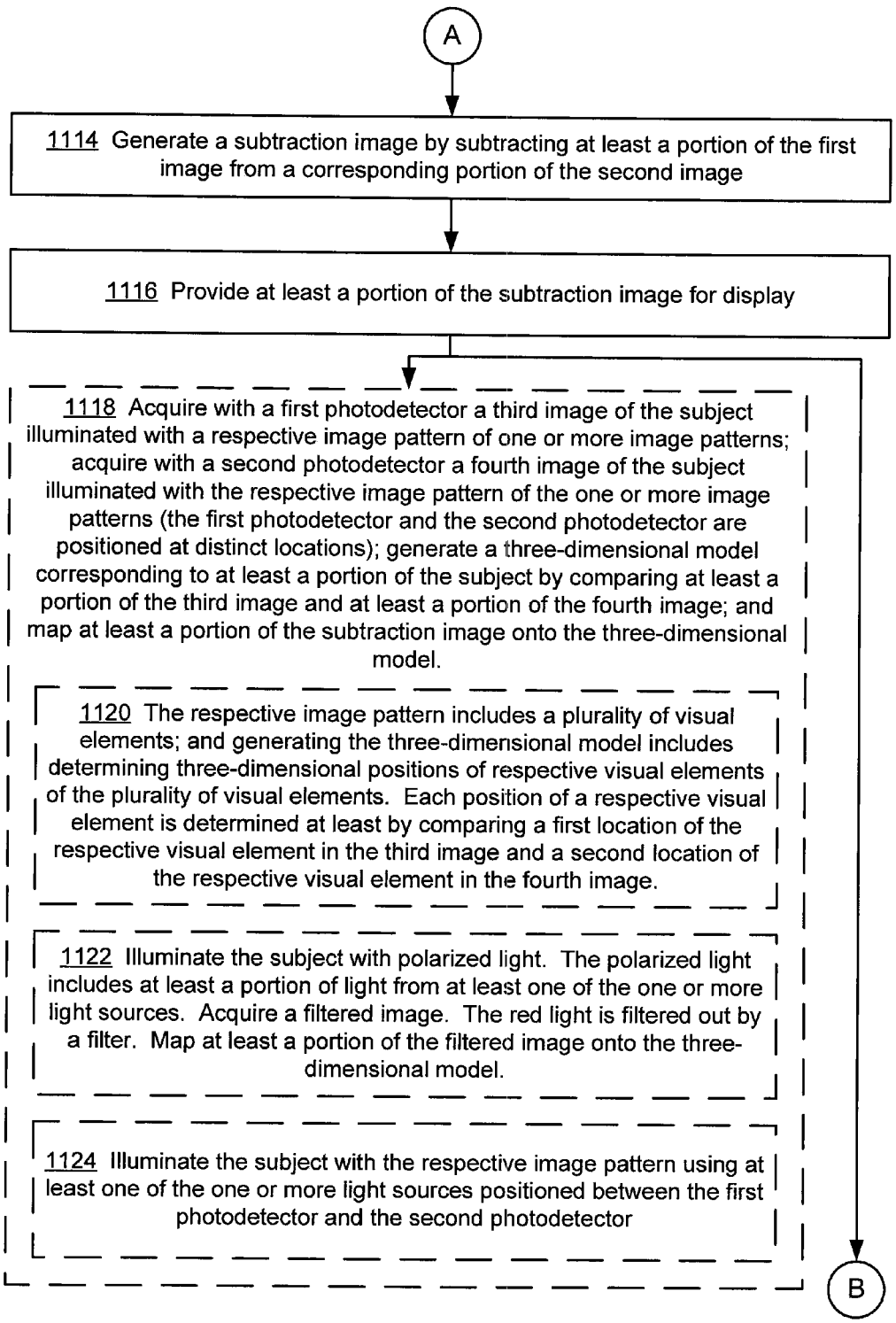

FIGS. 11A-11C are flow diagrams illustrating a method 1100 of imaging skin in accordance with some embodiments. The method 1100 is performed, for example, in the imaging system 200, 240, 300, 1000, 1020, or 1040 (FIGS. 2A-2B, 3, and 10A-10C).

In the method 1100, the imaging system illuminates (1102) a subject (e.g., the subject 202, FIGS. 2A-2C or the subject 1010, FIGS. 10A-10C) with at least one light source of one or more light sources (e.g., the light source 102, FIGS. 1A-1B; the light source 208, FIGS. 2A-2C; the light sources 208-1 and 208-2, FIG. 3; and the projectors 1012-1 and 1012-2, FIG. 10C).

In some embodiments, the one or more light sources include (1104) at least one polarizer to polarize light provided by at least one of the one or more light sources to illuminate the subject. In some embodiments, the one or more light sources provide polarized light without using a polarizer (e.g., an LED).

The imaging system acquires (1106) a first image of the subject in a first polarization with a respective photodetector of one or more photodetectors configured to acquire images of the subject as illuminated by the at least one light source.

The imaging system acquires (1108) a second image of the subject in a second polarization with the respective photodetector. Typically, the second polarization is perpendicular to the first polarization.

In connection with the operations 1106 and 1108, the following (1110 and 1112) provide additional details of the operations 1106 and 1108. In some embodiments, the subject is illuminated (1110) with light polarized in the first polarization. The first image of the subject in the first polarization is acquired with the respective photodetector while a respective adjustable polarizer coupled with the respective photodetector is configured to provide a first axis of polarization such that the respective adjustable polarizer transmits the light polarized in the first polarization (e.g., the first axis of polarization aligns with, or is parallel to, the first polarization), and the second image of the subject in the second polarization is acquired with the respective photodetector while the respective adjustable polarizer coupled with the respective photodetector is configured to provide a second axis of polarization distinct from the first axis of polarization such that the respective adjustable polarizer rejects the light polarized in the first polarization (e.g., the second axis of polarization is perpendicular to the first polarization). In other words, the imaging system acquires a parallel-polarization image as the first image, and a cross-polarization image as the second image.

Alternatively, in some embodiments, the subject is illuminated (1112) with light polarized in the first polarization. The first image of the subject in the first polarization is acquired with the respective photodetector while a respective adjustable polarizer coupled with the respective photodetector is configured to provide a first axis of polarization such that the respective adjustable polarizer rejects the light polarized in the first polarization (e.g., the first axis of polarization is perpendicular to the first polarization), and the second image of the subject in the second polarization is acquired with the respective photodetector while the respective adjustable polarizer coupled with the respective photodetector is configured to provide a second axis of polarization distinct from the first axis of polarization such that the respective adjustable polarizer transmits the light polarized in the first polarization (e.g., the second axis of polarization is parallel to the first polarization). In other words, the imaging system acquires a cross-polarization image as the first image, and a parallel-polarization image as the second image.

After acquiring the first and second images, the imaging system generates (1114, FIG. 11B) a subtraction image by subtracting at least a portion of the first image from a corresponding portion of the second image. In some embodiments, generating the subtraction image includes normalizing at least one of the first image and the second image. In some embodiments, normalizing the at least one of the first image and the second image includes one or more of: white balancing and color balancing. In some embodiments, the white balancing and/or the color balancing is performed using one or more color references (e.g., a standard color chart or a subset thereof) described above with respect to FIGS. 2A-2B. In some embodiments, generating the subtraction image includes adjusting at least one of the first image and the second image so that a registration error between the first image and the second image is reduced.

As explained above with respect to FIG. 1A, a parallel-polarization image typically has more contribution from light reflected from the surface of the subject (e.g., specular reflection) than a cross-polarization image. In comparison, a cross-polarization image generally has more contribution from light scattered from sub-surface layers of skin (e.g., subcutaneous tissues). Therefore, subtracting a parallel-polarization image from a cross-polarization image reduces the contribution from the specular reflection, and the resulting subtraction image can be used to show the properties of subcutaneous tissues. In contrast, subtracting a cross-polarization image from a parallel-polarization image reduces the contribution from light scattered from sub-surface layers, and the resulting subtraction image can be used to show the properties of the surface of skin.

The specular reflection from the surface of the subject can be used to determine the properties of the surface on the subject (e.g., the surface profile).

The imaging system provides (1116) at least a portion of the subtraction image for display. The at least a portion of the subtraction image may be provided as a two-dimensional image or a three-dimensional image mapped onto a three-dimensional model below with respect to operations 1118 and 1126 (FIGS. 11B and 11C).

In some embodiments, prior to mapping the subtraction image onto the three-dimensional model, the three-dimensional model is obtained. In some cases, the three-dimensional model is generated from at least two images. For example, in some embodiments, the imaging system acquires (1118) with a first photodetector a third image of the subject illuminated with a respective image pattern of one or more image patterns, and acquires with a second photodetector a fourth image of the subject illuminated with the respective image pattern of the one or more image patterns. Typically, the third image and the fourth image are acquired simultaneously (or the acquisition of the third image and the acquisition of the fourth image overlap in time). The first photodetector and the second photodetector are positioned at distinct locations (e.g., the imaging apparatuses 201-1 and 201-2 or the imaging apparatuses 201-2 and 201-3, FIG. 10C). The imaging system generates a three-dimensional model corresponding to at least a portion of the subject by comparing at least a portion of the third image and at least a portion of the fourth image. In some embodiments, the profile of the subject can be determined by performing triangulation with the third and fourth images. The respective image pattern is used to facilitate the triangulation, as described below with the operation 1120. The imaging system maps at least a portion of the subtraction image onto the three-dimensional model.

In some embodiments, the subject is illuminated with polarized light in the respective image pattern. The third image and the fourth image are acquired while the adjustable polarizers coupled with the first and second photodetectors are configured such that a respective polarization of each adjustable polarizer coupled with either the first or second photodetector is perpendicular to the polarization of the polarized light illuminating the subject. This reduces specular reflection from the subject, and thereby avoids over-saturation of an image with the specular reflection. This is particularly beneficial when the respective image pattern includes multiple colors.

In some embodiments, the respective image pattern includes (1120) a plurality of visual elements (e.g., dots, grids, meshes, squares, continuous or discrete images, or any combination thereof, in one or more colors) and generating the three-dimensional model includes determining three-dimensional positions of respective visual elements of the plurality of visual elements. In some embodiments, each visual element is identified based on one or more of: its color, shape, relative position to adjacent visual elements, and color and/or shape of adjacent visual elements. Each position of a respective visual element is determined at least by comparing a first location of the respective visual element in the third image and a second location of the respective visual element in the fourth image (e.g., performing triangulation based on the first location in the third image, the second location in the fourth image, and the locations and directions of the first and second photodetectors).

In some embodiments, the three-dimensional model includes a three-dimensional profile of the subject (e.g., a set of three-dimensional coordinates each corresponding to a reference point on the subject or a respective visual element as projected on the subject). In some embodiments, the three-dimensional model also includes colors and other properties of the skin.

In some embodiments, the three-dimensional model includes mapping information (e.g., a mapping function or a mapping table) so that a respective point on a respective image of the third and fourth images is mapped to the three-dimensional model. The mapping information may be used to project color from a respective two-dimensional image (e.g., any image acquired by the first or second photodetector) onto the three-dimensional model.

In some embodiments, the respective two-dimensional image is one of: (A) a diffuse white light image that is acquired with a respective photodetector while the subject is illuminated with a randomly-polarized light (e.g., from a fluorescent bulb) and the adjustable polarizer coupled with the respective photodetector is configured to reduce specular reflection; (B) a parallel-polarization image that is acquired with the respective photodetector while the subject is illuminated with polarized light and the adjustable polarizer coupled with the respective photodetector is configured to align with the polarization of the polarized light; (C) a cross-polarization image that is acquired with the respective photodetector while the subject is illuminated with polarized light and the adjustable polarizer coupled with the respective photodetector is configured to be perpendicular to the polarization of the polarized light; and (D) a filtered cross-polarization image that is acquired with the respective photodetector while the subject is illuminated with polarized light, the adjustable polarizer coupled with the respective photodetector is configured to be perpendicular to the polarization of the polarized light, and a filter is used to remove red light. Therefore, the imaging system may display the diffuse white light image, the parallel-polarization image, the cross-polarization image, and the filtered cross-polarization image as either two-dimensional images or three-dimensional images (as mapped onto the three-dimensional model). In some embodiments, the imaging system maps two or more two-dimensional images onto the three-dimensional model (e.g., diffuse white light images acquired with the first and second photodetectors). This often includes white balancing, color balancing, and intensity adjustment to ensure that there are no stitch marks along the junction of the two images as mapped onto the three-dimensional model. In some embodiments, the imaging system concurrently displays a plurality of the above-listed images.

In some embodiments, the imaging system illuminates (1122) the subject with polarized light. The polarized light includes at least a portion of light from at least one of the one or more light sources. For example, when the at least one of the one or more light sources provides unpolarized light (or randomly polarized light), a polarizer is used to transmit a portion of the light that is aligned with the orientation of the polarizer and block a portion of the light that is not aligned with the orientation of the polarizer. When the at least one of the one or more light sources provides polarized light, the polarized light from the at least one of the one or more light sources illuminates the subject. The imaging system acquires a filtered image. The red light is filtered out by a filter (e.g., the filter 105, FIG. 1B; and the filter 209, FIGS. 2A-2C). In some embodiments, the filter is used to filter the light from the at least one of the one or more light sources. In some embodiments, the filter is used to filter the light entering at least one of the first and second photodetectors. The imaging system maps at least a portion of the filtered image onto the three-dimensional model.

In some embodiments, the imaging system illuminates (1124) the subject with the respective image pattern using at least one of the one or more light sources positioned between the first photodetector and the second photodetector (e.g., the projector 1012-1 positioned between the photodetectors 201-1 and 201-2, or the projector 1012-2 positioned between the photodetectors 201-2 and 201-3, FIG. 10C).

Referring back to the operation 1116, in some cases, the three-dimensional model is generated from at least four images. For example, in some embodiments, the imaging system acquires (1126, FIG. 11C) with a first photodetector (e.g., the imaging apparatus 201-1, FIG. 10C) a third image of the subject illuminated with a first image pattern of one or more image patterns from a first light source (e.g., the projector 1012-1, FIG. 10C); acquires with a second photodetector (e.g., the imaging apparatus 201-2, FIG. 10C) a fourth image of the subject illuminated with the first image pattern of the one or more image patterns from the first light source; acquires with the second photodetector a fifth image of the subject illuminated with a second image pattern of the one or more image patterns from the second light source (e.g., the projector 1012-2, FIG. 10C); and acquires with a third photodetector (e.g., the imaging apparatus 201-3, FIG. 10C) a sixth image of the subject illuminated with the second image pattern of the one or more image patterns from the second light source. The first, second, and third photodetectors are positioned at distinct locations. In some embodiments, the second photodetector is positioned to acquire the frontal view of the subject and the first and third photodetectors are positioned to acquire each side view (e.g., the left side view and the right side view) of the subject. In some embodiments, the first, second, and third photodetectors are positioned such that the frontal view and each side view correspond to at least a same portion of the subject (e.g., a first portion of the subject in the frontal view acquired with the first photodetector and a second portion of the subject in the side view acquired with the second photodetector at least partially overlap). The imaging system generates a three-dimensional model corresponding to at least a portion of the subject by comparing at least a portion of the third image and at least a portion of the fourth image, and comparing at least a portion of the fifth image and at least a portion of the sixth image. In some embodiments, the imaging system generates a first portion of the three-dimensional model by comparing at least a portion of the third image and at least a portion of the fourth image, and a second portion of the three-dimensional model by comparing at least a portion of the fifth image and at least a portion of the sixth image. In some embodiments, the imaging system combines the first and second portions of the three-dimensional model to generate the three-dimensional model. The imaging system maps at least a portion of the subtraction image onto the three-dimensional model.

In some embodiments, the operation 1126 includes: illuminating the subject with the first image pattern from the first light source without illuminating the subject with the second light source; simultaneously acquiring the third image of the subject with the first photodetector and the fourth image of the subject with the second photodetector (i.e., the acquisition of the third image and the acquisition of the fourth image at least partially overlap in time) while the subject is illuminated by the first light source; illuminating the subject with the second image pattern from the second light source without illuminating the subject with the first light source; and simultaneously acquiring the fifth image of the subject with the second detector and the sixth image of the subject with the third detector (i.e., the acquisition of the fifth image and the acquisition of the sixth image at least partially overlap in time) while the subject is illuminated by the second light source.

In some embodiments, the operation 1126 includes: simultaneously illuminating the subject with the first image pattern from the first light source and the second image pattern from the second light source; and simultaneously acquiring the images with the first, second, and third photodetectors. In some embodiments, the photodetectors and the light sources are positioned such that the illumination on the subject by the first light source does not overlap with the illumination on the subject by the second light source. In some embodiments, the first image pattern is distinct from the second image pattern such that visual elements in the first image pattern are discernible from visual elements in the second image pattern (e.g., based on the color, shape, spacing, etc.) even when the first image pattern illuminated on the subject by the first light source overlaps with the second image pattern illuminated on the subject by the second light source. In such embodiments, the imaging system generates the three-dimensional model by comparing the image acquired with the first photodetector and the image acquired with the second photodetector, and comparing the image acquired with the second photodetector and the image acquired with the third photodetector.

Note that details of the operations 1118-1124 described above are also applicable in an analogous manner to the operation 1126. For brevity, these details are not repeated herein.

In some embodiments, the first image pattern and the second image pattern are (1128) identical.

The foregoing description, for purpose of explanation, has been described with reference to specific embodiments. However, the illustrative discussions above are not intended to be exhaustive or to limit the inventions to the precise forms disclosed. Many modifications and variations are possible in view of the above teachings. The embodiments were chosen and described in order to best explain the principles of the inventions and their practical applications, to thereby enable others skilled in the art to best utilize the inventions and various embodiments with various modifications as are suited to the particular use contemplated.

What is claimed is:

1. An imaging system for imaging skin, comprising:
   one or more light sources configured to illuminate a subject;
   one or more photodetectors configured to acquire images of the subject as illuminated by at least one of the one or more light sources;
   one or more adjustable polarizers, each coupled with a respective photodetector of the one or more photodetectors and configured to provide an adjustable axis of polarization of light received by the respective photodetector;
   one or more processors; and
   memory storing one or more programs for execution by the one or more processors, the one or more programs including instructions for:
      acquiring a first image of the subject in a first polarization with the respective photodetector;
      acquiring a second image of the subject in a second polarization with the respective photodetector;
      generating a subtraction image by subtracting at least a portion of the first image from a corresponding portion of the second image; and
      providing at least a portion of the subtraction image for display.

2. The system of claim 1, wherein the one or more light sources include at least one polarizer to polarize light provided by at least one of the one or more light sources to illuminate the subject.

3. The system of claim 1, wherein:
the subject is illuminated with light polarized in the first polarization;
the first image of the subject in the first polarization is acquired with the respective photodetector while a respective adjustable polarizer coupled with the respective photodetector is configured to provide a first axis of polarization such that the respective adjustable polarizer transmits the light polarized in the first polarization; and
the second image of the subject in the second polarization is acquired with the respective photodetector while the respective adjustable polarizer coupled with the respective photodetector is configured to provide a second axis of polarization distinct from the first axis of polarization such that the respective adjustable polarizer rejects the light polarized in the first polarization.

4. The system of claim 1, wherein:
the subject is illuminated with light polarized in the first polarization;
the first image of the subject in the first polarization is acquired with the respective photodetector while a respective adjustable polarizer coupled with the respective photodetector is configured to provide a first axis of polarization such that the respective adjustable polarizer rejects the light polarized in the first polarization; and
the second image of the subject in the second polarization is acquired with the respective photodetector while the respective adjustable polarizer coupled with the respective photodetector is configured to provide a second axis of polarization distinct from the first axis of polarization such that the respective adjustable polarizer transmits the light polarized in the first polarization.

5. The system of claim 1, wherein:
at least one of the one or more light sources is configured to illuminate the subject with one or more image patterns;
the system includes a first photodetector and a second photodetector to acquire images of the subject, wherein the first photodetector and the second photodetector are positioned at distinct locations; and
the one or more programs include instructions for:
acquiring with the first photodetector a third image of the subject illuminated with a respective image pattern of the one or more image patterns;
acquiring with the second photodetector a fourth image of the subject illuminated with the respective image pattern of the one or more image patterns;
generating a three-dimensional model corresponding to at least a portion of the subject by comparing at least a portion of the third image and at least a portion of the fourth image; and
mapping at least a portion of the subtraction image onto the three-dimensional model.

6. The system of claim 5, wherein:
the respective image pattern includes a plurality of visual elements; and
the instructions for generating the three-dimensional model include determining three-dimensional positions of respective visual elements of the plurality of visual elements, wherein each position of a respective visual element is determined at least by comparing a first location of the respective visual element in the third image and a second location of the respective visual element in the fourth image.

7. The system of claim 5, further comprising a filter to filter out red light, wherein
the one or more programs include instructions for:
illuminating the subject with polarized light, the polarized light including at least a portion of light from at least one of the one or more light sources;
acquiring a filtered image, wherein the red light is filtered out by the filter; and
mapping at least a portion of the filtered image onto the three-dimensional model.

8. The system of claim 5, wherein the at least one of the one or more light sources configured to illuminate the subject with one or more image patterns is positioned between the first photodetector and the second photodetector.

9. The system of claim 1, wherein
a first light source and a second light source configured to illuminate the subject with one or more image patterns;
the system includes a first photodetector, a second photodetector, and a third photodetector to acquire images of the subject, wherein the first photodetector, the second photodetector, and the third photodetector are positioned at distinct locations; and
the one or more programs include instructions for:
acquiring with the first photodetector a third image of the subject illuminated with a first image pattern of the one or more image patterns from the first light source;
acquiring with the second photodetector a fourth image of the subject illuminated with the first image pattern of the one or more image patterns from the first light source;
acquiring with the second photodetector a fifth image of the subject illuminated with a second image pattern of the one or more image patterns from the second light source;
acquiring with the third photodetector a sixth image of the subject illuminated with the second image pattern of the one or more image patterns from the second light source;
generating a three-dimensional model corresponding to at least a portion of the subject by comparing at least a portion of the third image and at least a portion of the fourth image, and comparing at least a portion of the fifth image and at least a portion of the sixth image; and
mapping at least a portion of the subtraction image onto the three-dimensional model.

10. The system of claim 9, wherein the first image pattern and the second image pattern are identical.

11. A method for imaging skin, performed by a system including one or more processors and memory storing one or more programs for execution by the one or more processors, the method comprising:
illuminating a subject with at least one light source of one or more light sources;
acquiring a first image of the subject in a first polarization with a respective photodetector of one or more photodetectors configured to acquire images of the subject as illuminated by the at least one light source;
acquiring a second image of the subject in a second polarization with the respective photodetector;
generating, by the one or more processors of the system, a subtraction image by subtracting at least a portion of the first image from a corresponding portion of the second image; and
providing at least a portion of the subtraction image for display.

12. The method of claim 11, wherein the one or more light sources include at least one polarizer to polarize light provided by at least one of the one or more light sources to illuminate the subject.

13. The method of claim 11, wherein:
the subject is illuminated with light polarized in the first polarization;
the first image of the subject in the first polarization is acquired with the respective photodetector while a respective adjustable polarizer coupled with the respective photodetector is configured to provide a first axis of polarization such that the respective adjustable polarizer transmits the light polarized in the first polarization; and
the second image of the subject in the second polarization is acquired with the respective photodetector while the respective adjustable polarizer coupled with the respective photodetector is configured to provide a second axis of polarization distinct from the first axis of polarization such that the respective adjustable polarizer rejects the light polarized in the first polarization.

14. The method of claim 11, wherein:
the subject is illuminated with light polarized in the first polarization;
the first image of the subject in the first polarization is acquired with the respective photodetector while a respective adjustable polarizer coupled with the respective photodetector is configured to provide a first axis of polarization such that the respective adjustable polarizer rejects the light polarized in the first polarization; and
the second image of the subject in the second polarization is acquired with the respective photodetector while the respective adjustable polarizer coupled with the respective photodetector is configured to provide a second axis of polarization distinct from the first axis of polarization such that the respective adjustable polarizer transmits the light polarized in the first polarization.

15. The method of claim 11, further comprising:
acquiring with a first photodetector a third image of the subject illuminated with a respective image pattern of one or more image patterns;
acquiring with a second photodetector a fourth image of the subject illuminated with the respective image pattern of the one or more image patterns, wherein the first photodetector and the second photodetector are positioned at distinct locations;
generating a three-dimensional model corresponding to at least a portion of the subject by comparing at least a portion of the third image and at least a portion of the fourth image; and
mapping at least a portion of the subtraction image onto the three-dimensional model.

16. The method of claim 15, wherein:
the respective image pattern includes a plurality of visual elements; and
generating the three-dimensional model includes determining three-dimensional positions of respective visual elements of the plurality of visual elements, wherein each position of a respective visual element is determined at least by comparing a first location of the respective visual element in the third image and a second location of the respective visual element in the fourth image.

17. The method of claim 15, further comprising:
illuminating the subject with polarized light, the polarized light including at least a portion of light from at least one of the one or more light sources;
acquiring a filtered image, wherein the red light is filtered out by a filter; and
mapping at least a portion of the filtered image onto the three-dimensional model.

18. The method of claim 15, including illuminating the subject with the respective image pattern using at least one of the one or more light sources positioned between the first photodetector and the second photodetector.

19. The method of claim 11, wherein
acquiring with a first photodetector a third image of the subject illuminated with a first image pattern of one or more image patterns from a first light source;
acquiring with a second photodetector a fourth image of the subject illuminated with the first image pattern of the one or more image patterns from the first light source;
acquiring with the second photodetector a fifth image of the subject illuminated with a second image pattern of the one or more image patterns from the second light source;
acquiring with a third photodetector a sixth image of the subject illuminated with the second image pattern of the one or more image patterns from the second light source;
generating a three-dimensional model corresponding to at least a portion of the subject by comparing at least a portion of the third image and at least a portion of the fourth image, and comparing at least a portion of the fifth image and at least a portion of the sixth image; and
mapping at least a portion of the subtraction image onto the three-dimensional model.

20. The method of claim 19, wherein the first image pattern and the second image pattern are identical.

\* \* \* \* \*